US008864827B2

(12) United States Patent
Ek

(10) Patent No.: US 8,864,827 B2
(45) Date of Patent: *Oct. 21, 2014

(54) SYSTEM AND METHOD FOR JOINT RESURFACE REPAIR

(75) Inventor: Steven W. Ek, Bolton, MA (US)

(73) Assignee: Arthrosurface Inc., Franklin, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/470,678

(22) Filed: May 14, 2012

(65) Prior Publication Data

US 2012/0271417 A1 Oct. 25, 2012

Related U.S. Application Data

(63) Continuation of application No. 12/027,121, filed on Feb. 6, 2008, now Pat. No. 8,177,841, and a continuation-in-part of application No. 11/359,891, filed on Feb. 22, 2006, now Pat. No. 7,713,305, which is a continuation-in-part of application No. 10/373,463, filed on Feb. 24, 2003, now Pat. No. 7,678,151, which is a continuation-in-part of application No. 10/162,533, filed on Jun. 4, 2002, now Pat. No. 6,679,917, which is a continuation-in-part of application No. 10/024,077, filed on Dec. 17, 2001, now Pat. No. 6,610,067, which is a continuation-in-part of application No. 09/846,657, filed on May 1, 2001, now Pat. No. 6,520,964.

(60) Provisional application No. 60/888,382, filed on Feb. 6, 2007, provisional application No. 60/201,049, filed on May 1, 2000.

(51) Int. Cl.
| | |
|---|---|
| *A61F 2/08* | (2006.01) |
| *A61B 17/56* | (2006.01) |
| *A61B 17/16* | (2006.01) |
| *A61F 2/30* | (2006.01) |
| *A61F 2/38* | (2006.01) |
| *A61F 2/46* | (2006.01) |

(52) U.S. Cl.
CPC ......... *A61F 17/1764* (2013.01); *A61F 2/30942* (2013.01); *A61F 2002/30116* (2013.01); *A61F 2230/0006* (2013.01); *A61F 2002/3895* (2013.01); *A61F 2002/30112* (2013.01); *A61F 2002/3085* (2013.01); *A61F 2002/30878* (2013.01); *A61F 2/3859* (2013.01); *A61F 2250/0062* (2013.01); *A61B 17/1635* (2013.01); *A61F 2002/30607* (2013.01); *A61F 2002/4663* (2013.01); *A61F 2002/4658* (2013.01); *A61F 2/30756* (2013.01); *A61F 2230/0004* (2013.01); *A61F 2/4657* (2013.01)
USPC ............. 623/14.12; 606/102; 606/80; 606/96

(58) Field of Classification Search
CPC . A61F 2/30756; A61F 2/3859; A61F 2/4657; A61F 2250/0062; A61F 2/30942; A61F 2002/30112; A61F 2002/30116; A61F 2002/30607; A61F 2002/3085; A61F 2002/30878; A61F 2002/3895; A61F 2002/4658; A61F 2002/4663; A61F 2230/0004; A61F 2230/0006; A61B 17/1764; A61B 17/1635
USPC .......... 623/14.12, 20.31, 20.14, 20.32, 20.35, 623/20.3, 20.36, 908; 606/80, 96, 102
See application file for complete search history.

(56) References Cited

U.S. PATENT DOCUMENTS

| 103,645 A | 5/1870 | Muscroft |
| 992,819 A | 5/1911 | Springer |

(Continued)

FOREIGN PATENT DOCUMENTS

| AU | 2001262308 | 12/2001 |
| AU | 2001259327 B2 | 2/2005 |

(Continued)

OTHER PUBLICATIONS

International Search Report and Written Opinion dated Aug. 8, 2007 issued in corresponding PCT patent application No. PCT/US06/29875.

(Continued)

*Primary Examiner* — Pedro Philogene
(74) *Attorney, Agent, or Firm* — Grossman Tucker Perreault & Pfleger PLLC

(57) ABSTRACT

An implant comprising a first, second, and third segment wherein the second and third segments partially overlap the first segment and define a load bearing surface comprising an anterior-posterior (AP) curvature including at least two tangential curves of the portion of the articular surface of the femoral condyle, the tangential curves having different radii of curvature. A drill guide comprises a body portion including a first, second and third bushing spaced along the body portion to establish a first, second and third axes, respectively. Each axis may be substantially normal to the articular surface at three different points along a curvature of the articular surface comprising the two tangential curves. A measuring device comprises a housing defining a longitudinally passageway and an outrigger. A guide pin may be received in the longitudinal passageway and a measuring device determines how far the guide pin is in the passageway.

42 Claims, 7 Drawing Sheets

(56) References Cited

U.S. PATENT DOCUMENTS

| | | | |
|---|---|---|---|
| 1,451,610 A | 4/1923 | Gestas | |
| 2,267,925 A | 12/1941 | Johnston | |
| 2,379,984 A | 7/1943 | Nereaux | |
| 2,381,102 A | 10/1943 | Boyd | |
| 2,570,465 A | 10/1951 | Lundholm | |
| 3,176,395 A | 4/1965 | Watner et al. | |
| 3,715,763 A | 2/1973 | Link | |
| 3,840,905 A | 10/1974 | Deane | |
| 3,852,830 A | 12/1974 | Marmor | |
| 4,016,651 A | 4/1977 | Kawahara et al. | |
| 4,016,874 A | 4/1977 | Maffei et al. | |
| 4,034,418 A | 7/1977 | Jackson et al. | |
| 4,044,464 A | 8/1977 | Schiess et al. | |
| 4,158,894 A | 6/1979 | Worrell | |
| 4,319,577 A | 3/1982 | Bofinger et al. | |
| 4,330,891 A | 5/1982 | Brånemark et al. | |
| 4,340,978 A * | 7/1982 | Buechel et al. | 623/20.29 |
| 4,344,192 A | 8/1982 | Imbert | |
| 4,433,687 A | 2/1984 | Burke et al. | |
| 4,462,120 A | 7/1984 | Rambert et al. | |
| 4,474,177 A | 10/1984 | Whiteside | |
| 4,484,570 A | 11/1984 | Sutter et al. | |
| 4,531,517 A | 7/1985 | Forte et al. | |
| 4,535,768 A | 8/1985 | Hourahane et al. | |
| 4,565,768 A | 1/1986 | Nonogaki et al. | |
| 4,634,720 A | 1/1987 | Dorman et al. | |
| 4,655,752 A | 4/1987 | Honkanen et al. | |
| 4,661,536 A | 4/1987 | Dorman et al. | |
| 4,662,371 A | 5/1987 | Whipple et al. | |
| 4,664,669 A | 5/1987 | Ohyabu et al. | |
| 4,673,407 A | 6/1987 | Martin | |
| 4,693,986 A | 9/1987 | Vit et al. | |
| 4,708,139 A | 11/1987 | Dunbar, IV | |
| 4,712,545 A | 12/1987 | Honkanen | |
| 4,714,478 A | 12/1987 | Fischer | |
| 4,719,908 A | 1/1988 | Averill et al. | |
| 4,722,331 A | 2/1988 | Fox | |
| 4,729,761 A | 3/1988 | White | |
| 4,781,182 A | 11/1988 | Purnell et al. | |
| 4,788,970 A | 12/1988 | Karas et al. | |
| 4,823,780 A | 4/1989 | Odensten et al. | |
| 4,842,604 A | 6/1989 | Dorman et al. | |
| 4,896,663 A | 1/1990 | Vandewalls | |
| 4,911,153 A | 3/1990 | Border | |
| 4,911,720 A | 3/1990 | Collier | |
| 4,920,958 A | 5/1990 | Walt et al. | |
| 4,927,421 A | 5/1990 | Goble et al. | |
| 4,936,853 A | 6/1990 | Fabian et al. | |
| 4,938,778 A | 7/1990 | Ohyabu et al. | |
| 4,940,467 A | 7/1990 | Tronzo | |
| 4,945,904 A | 8/1990 | Bolton et al. | |
| 4,976,037 A | 12/1990 | Hines | |
| 4,978,258 A | 12/1990 | Lins | |
| 4,979,957 A | 12/1990 | Hodorek | |
| 4,989,110 A | 1/1991 | Zevin et al. | |
| 4,990,163 A | 2/1991 | Ducheyne et al. | |
| 4,997,434 A | 3/1991 | Seedhom et al. | |
| 4,998,938 A | 3/1991 | Ghajar et al. | |
| 5,007,930 A | 4/1991 | Dorman et al. | |
| 5,019,104 A | 5/1991 | Whiteside et al. | |
| 5,053,049 A | 10/1991 | Campbell | |
| 5,092,895 A * | 3/1992 | Albrektsson et al. | 623/20.3 |
| 5,100,405 A | 3/1992 | McLaren | |
| 5,127,413 A | 7/1992 | Ebert | |
| 5,127,920 A | 7/1992 | MacArthur | |
| 5,154,720 A | 10/1992 | Trott et al. | |
| 5,180,384 A | 1/1993 | Mikhail | |
| 5,192,291 A | 3/1993 | Pannek, Jr. | |
| 5,201,881 A | 4/1993 | Evans | |
| 5,207,753 A | 5/1993 | Badrinath | |
| 5,211,647 A | 5/1993 | Schmieding | |
| 5,224,945 A | 7/1993 | Pannek, Jr. | |
| 5,234,435 A | 8/1993 | Seagrave, Jr. | |
| 5,255,838 A | 10/1993 | Gladdish, Jr. et al. | |
| 5,263,498 A | 11/1993 | Caspari et al. | |
| 5,263,987 A | 11/1993 | Shah | |
| 5,282,863 A | 2/1994 | Burton | |
| 5,290,313 A | 3/1994 | Heldreth | |
| 5,312,411 A | 5/1994 | Steele | |
| 5,314,478 A | 5/1994 | Oka et al. | |
| 5,314,482 A | 5/1994 | Goodfellow et al. | |
| 5,324,295 A | 6/1994 | Shapiro | |
| 5,326,366 A | 7/1994 | Pascarella et al. | |
| 5,336,224 A | 8/1994 | Selman | |
| 5,354,300 A | 10/1994 | Goble et al. | |
| 5,358,525 A | 10/1994 | Fox et al. | |
| 5,360,446 A | 11/1994 | Kennedy | |
| 5,374,270 A | 12/1994 | McGuire et al. | |
| 5,383,937 A | 1/1995 | Mikhail | |
| 5,387,218 A | 2/1995 | Meswania | |
| 5,395,401 A | 3/1995 | Bahler | |
| 5,409,490 A | 4/1995 | Ethridge | |
| 5,409,494 A | 4/1995 | Morgan | |
| 5,413,608 A | 5/1995 | Keller | |
| 5,423,822 A | 6/1995 | Hershberger | |
| 5,423,823 A | 6/1995 | Schmieding | |
| 5,425,733 A | 6/1995 | Schmieding | |
| 5,458,643 A | 10/1995 | Oka et al. | |
| 5,480,443 A | 1/1996 | Elias | |
| 5,486,178 A | 1/1996 | Hodge | |
| 5,509,918 A | 4/1996 | Romano | |
| 5,520,695 A | 5/1996 | Luckman | |
| 5,522,900 A | 6/1996 | Hollister | |
| 5,534,031 A | 7/1996 | Matsuzaki et al. | |
| 5,540,696 A | 7/1996 | Booth, Jr. et al. | |
| 5,562,664 A | 10/1996 | Durlacher et al. | |
| 5,580,353 A | 12/1996 | Mendes et al. | |
| 5,591,170 A | 1/1997 | Spievack et al. | |
| 5,593,450 A | 1/1997 | Scott et al. | |
| 5,595,193 A | 1/1997 | Walus et al. | |
| 5,597,273 A | 1/1997 | Hirsch | |
| 5,601,550 A | 2/1997 | Esser | |
| 5,607,480 A | 3/1997 | Beaty | |
| 5,616,146 A | 4/1997 | Murray | |
| 5,620,055 A | 4/1997 | Javerlhac | |
| 5,624,463 A | 4/1997 | Stone et al. | |
| 5,632,745 A | 5/1997 | Schwartz | |
| 5,634,927 A | 6/1997 | Houston et al. | |
| 5,645,598 A | 7/1997 | Brosnahan, III | |
| 5,681,311 A | 10/1997 | Foley et al. | |
| 5,681,320 A | 10/1997 | McGuire | |
| 5,682,886 A | 11/1997 | Delp et al. | |
| 5,683,400 A | 11/1997 | McGuire | |
| 5,683,465 A | 11/1997 | Shinn et al. | |
| 5,683,466 A | 11/1997 | Vitale | |
| 5,700,264 A | 12/1997 | Zucherman et al. | |
| 5,700,265 A | 12/1997 | Romano | |
| 5,702,401 A | 12/1997 | Shaffer | |
| 5,702,465 A | 12/1997 | Burkinshaw | |
| 5,702,467 A | 12/1997 | Gabriel et al. | |
| 5,741,266 A | 4/1998 | Moran et al. | |
| 5,765,973 A | 6/1998 | Hirsch et al. | |
| 5,769,855 A | 6/1998 | Bertin et al. | |
| 5,769,899 A | 6/1998 | Schwartz et al. | |
| 5,771,310 A | 6/1998 | Vannah | |
| 5,776,137 A | 7/1998 | Katz | |
| 5,782,835 A | 7/1998 | Hart et al. | |
| 5,800,440 A | 9/1998 | Stead | |
| 5,810,851 A | 9/1998 | Yoon | |
| 5,816,811 A | 10/1998 | Beaty | |
| 5,817,095 A | 10/1998 | Smith | |
| 5,824,087 A | 10/1998 | Aspden et al. | |
| 5,824,105 A | 10/1998 | Ries et al. | |
| RE36,020 E | 12/1998 | Moore et al. | |
| 5,882,350 A | 3/1999 | Ralph et al. | |
| 5,885,297 A | 3/1999 | Matsen, III | |
| 5,885,298 A | 3/1999 | Herrington et al. | |
| 5,888,210 A | 3/1999 | Draenert | |
| 5,893,889 A | 4/1999 | Harrington | |
| 5,895,390 A | 4/1999 | Moran et al. | |
| 5,911,126 A | 6/1999 | Massen | |
| 5,918,604 A | 7/1999 | Whelan | |
| 5,919,196 A | 7/1999 | Bobic et al. | |
| 5,928,239 A | 7/1999 | Mirza | |

(56) References Cited

U.S. PATENT DOCUMENTS

| | | | |
|---|---|---|---|
| 5,928,241 A | 7/1999 | Menut et al. |
| 5,928,286 A | 7/1999 | Ashby et al. |
| 5,964,752 A | 10/1999 | Stone |
| 5,964,768 A | 10/1999 | Huebner |
| 5,964,808 A | 10/1999 | Blaha et al. |
| 5,968,050 A | 10/1999 | Torrie |
| 5,989,269 A | 11/1999 | Vibe-Hansen et al. |
| 5,990,382 A | 11/1999 | Fox |
| 5,997,543 A | 12/1999 | Truscott |
| 5,997,582 A | 12/1999 | Weiss |
| 6,004,323 A | 12/1999 | Park et al. |
| 6,010,502 A | 1/2000 | Bagby |
| 6,015,411 A | 1/2000 | Ohkoshi et al. |
| 6,017,348 A | 1/2000 | Hart et al. |
| 6,019,767 A | 2/2000 | Howell |
| 6,019,790 A | 2/2000 | Holmberg et al. |
| 6,045,554 A | 4/2000 | Grooms et al. |
| 6,045,564 A | 4/2000 | Walen |
| 6,052,909 A | 4/2000 | Gardner |
| 6,059,831 A | 5/2000 | Braslow |
| 6,071,310 A | 6/2000 | Picha et al. |
| 6,081,741 A | 6/2000 | Hollis |
| 6,086,593 A | 7/2000 | Bonutti |
| 6,086,614 A | 7/2000 | Mumme |
| 6,102,948 A | 8/2000 | Brosnahan, III |
| 6,120,511 A | 9/2000 | Chan |
| 6,120,542 A | 9/2000 | Camino et al. |
| 6,132,433 A | 10/2000 | Whelan |
| 6,146,385 A | 11/2000 | Torrie et al. |
| 6,149,654 A | 11/2000 | Johnson |
| 6,152,960 A * | 11/2000 | Pappas ................ 623/20.31 |
| 6,159,216 A | 12/2000 | Burkinshaw et al. |
| 6,165,223 A | 12/2000 | Metzger et al. |
| 6,168,626 B1 | 1/2001 | Hyon et al. |
| 6,171,340 B1 * | 1/2001 | McDowell ................ 623/18.11 |
| 6,193,724 B1 | 2/2001 | Chan |
| 6,206,885 B1 | 3/2001 | Ghahremani et al. |
| 6,206,926 B1 * | 3/2001 | Pappas ................ 623/20.27 |
| 6,217,549 B1 | 4/2001 | Selmon et al. |
| 6,217,619 B1 | 4/2001 | Keller |
| 6,235,060 B1 | 5/2001 | Kubein-Meesenburg et al. |
| 6,251,143 B1 | 6/2001 | Schwartz et al. |
| 6,254,605 B1 | 7/2001 | Howell |
| 6,270,347 B1 | 8/2001 | Webster et al. |
| 6,280,474 B1 | 8/2001 | Cassidy et al. |
| 6,299,645 B1 | 10/2001 | Ogden |
| 6,299,648 B1 | 10/2001 | Doubler et al. |
| 6,306,142 B1 | 10/2001 | Johanson et al. |
| 6,310,116 B1 | 10/2001 | Yasuda et al. |
| 6,315,798 B1 | 11/2001 | Ashby et al. |
| 6,322,500 B1 | 11/2001 | Sikora et al. |
| 6,328,752 B1 | 12/2001 | Sjostrom et al. |
| 6,342,075 B1 | 1/2002 | MacArthur |
| 6,358,251 B1 | 3/2002 | Mirza |
| 6,358,253 B1 | 3/2002 | Torrie et al. |
| 6,364,910 B1 | 4/2002 | Shultz et al. |
| 6,375,658 B1 | 4/2002 | Hangody et al. |
| 6,383,188 B2 | 5/2002 | Kuslich |
| 6,415,516 B1 | 7/2002 | Tirado et al. |
| 6,416,518 B1 | 7/2002 | DeMayo |
| 6,443,954 B1 | 9/2002 | Bramlet et al. |
| 6,451,023 B1 | 9/2002 | Salazar et al. |
| 6,461,373 B2 | 10/2002 | Wyman et al. |
| 6,468,309 B1 | 10/2002 | Lieberman |
| 6,478,801 B1 | 11/2002 | Ralph et al. |
| 6,478,822 B1 | 11/2002 | Leroux et al. |
| 6,482,210 B1 | 11/2002 | Skiba et al. |
| 6,494,914 B2 | 12/2002 | Brown et al. |
| 6,520,964 B2 | 2/2003 | Tallarida et al. |
| 6,527,754 B1 | 3/2003 | Tallarida et al. |
| 6,530,956 B1 | 3/2003 | Mansmann |
| 6,540,786 B2 | 4/2003 | Chibrac et al. |
| 6,551,322 B1 | 4/2003 | Lieberman |
| 6,554,866 B1 | 4/2003 | Aicher et al. |
| 6,575,980 B1 | 6/2003 | Robie et al. |
| 6,575,982 B1 | 6/2003 | Bonutti |
| 6,585,666 B2 | 7/2003 | Suh et al. |
| 6,591,581 B2 | 7/2003 | Schmieding |
| 6,599,321 B2 | 7/2003 | Hyde et al. |
| 6,602,258 B1 | 8/2003 | Katz |
| 6,607,561 B2 | 8/2003 | Brannon |
| 6,610,067 B2 | 8/2003 | Tallarida |
| 6,610,095 B1 | 8/2003 | Pope et al. |
| 6,623,474 B1 | 9/2003 | Ponzi |
| 6,626,950 B2 | 9/2003 | Brown et al. |
| 6,629,997 B2 | 10/2003 | Mansmann |
| 6,632,246 B1 | 10/2003 | Simon et al. |
| 6,679,917 B2 | 1/2004 | Ek |
| 6,746,451 B2 | 6/2004 | Middleton et al. |
| 6,755,837 B2 | 6/2004 | Ebner |
| 6,755,865 B2 | 6/2004 | Tarabishy |
| 6,770,078 B2 | 8/2004 | Bonutti |
| 6,783,550 B2 | 8/2004 | MacArthur |
| 6,783,551 B1 | 8/2004 | Metzger |
| 6,802,864 B2 | 10/2004 | Tornier |
| 6,814,735 B1 | 11/2004 | Zirngibl |
| 6,827,722 B1 | 12/2004 | Schoenefeld |
| 6,860,902 B2 | 3/2005 | Reiley |
| 6,884,246 B1 | 4/2005 | Sonnabend et al. |
| 6,884,621 B2 | 4/2005 | Liao et al. |
| 6,893,467 B1 | 5/2005 | Bercovy |
| 6,923,813 B2 | 8/2005 | Phillips et al. |
| 6,926,739 B1 | 8/2005 | OConnor |
| 6,951,538 B2 | 10/2005 | Ritland |
| 6,953,478 B2 | 10/2005 | Bouttens et al. |
| 6,962,577 B2 | 11/2005 | Tallarida et al. |
| 6,969,393 B2 | 11/2005 | Pinczewski et al. |
| 6,984,248 B2 | 1/2006 | Hyde, Jr. |
| 6,989,016 B2 | 1/2006 | Tallarida et al. |
| 7,029,479 B2 | 4/2006 | Tallarida |
| 7,048,767 B2 | 5/2006 | Namavar |
| 7,063,717 B2 | 6/2006 | St. Pierre et al. |
| 7,112,205 B2 | 9/2006 | Carrison |
| 7,115,131 B2 | 10/2006 | Engh et al. |
| 7,118,578 B2 | 10/2006 | West, Jr. et al. |
| 7,156,880 B2 | 1/2007 | Evans et al. |
| 7,160,305 B2 | 1/2007 | Schmieding |
| 7,163,541 B2 | 1/2007 | Ek |
| 7,166,133 B2 | 1/2007 | Evans et al. |
| 7,192,431 B2 | 3/2007 | Hangody et al. |
| 7,192,432 B2 | 3/2007 | Wetzler et al. |
| 7,204,839 B2 | 4/2007 | Dreyfuss et al. |
| 7,204,854 B2 | 4/2007 | Guederian et al. |
| 7,235,107 B2 | 6/2007 | Evans et al. |
| 7,238,189 B2 | 7/2007 | Schmieding et al. |
| 7,241,316 B2 | 7/2007 | Evans et al. |
| 7,264,634 B2 | 9/2007 | Schmieding |
| 7,290,347 B2 | 11/2007 | Augostino et al. |
| 7,303,577 B1 | 12/2007 | Dean |
| 7,311,702 B2 | 12/2007 | Tallarida et al. |
| 7,361,195 B2 | 4/2008 | Schwartz et al. |
| 7,368,065 B2 | 5/2008 | Yang et al. |
| 7,371,260 B2 | 5/2008 | Malinin |
| 7,462,199 B2 | 12/2008 | Justin et al. |
| 7,468,075 B2 | 12/2008 | Lang et al. |
| 7,476,250 B1 | 1/2009 | Mansmann |
| 7,491,235 B2 | 2/2009 | Fell |
| 7,501,073 B2 | 3/2009 | Wen et al. |
| 7,510,558 B2 | 3/2009 | Tallarida |
| 7,531,000 B2 | 5/2009 | Hodorek |
| 7,559,932 B2 | 7/2009 | Truckai et al. |
| 7,569,059 B2 | 8/2009 | Cerundolo |
| 7,572,291 B2 | 8/2009 | Gil et al. |
| 7,575,578 B2 | 8/2009 | Wetzler et al. |
| 7,578,824 B2 | 8/2009 | Justin et al. |
| 7,604,641 B2 | 10/2009 | Tallarida et al. |
| 7,611,653 B2 | 11/2009 | Elsner et al. |
| 7,618,451 B2 | 11/2009 | Berez et al. |
| 7,618,462 B2 | 11/2009 | Ek |
| 7,632,294 B2 | 12/2009 | Milbodker et al. |
| 7,641,658 B2 | 1/2010 | Shaolian et al. |
| 7,641,689 B2 | 1/2010 | Fell et al. |
| 7,670,381 B2 | 3/2010 | Schwartz |
| 7,678,151 B2 | 3/2010 | Ek |

(56) References Cited

U.S. PATENT DOCUMENTS

| | | |
|---|---|---|
| 7,682,540 B2 | 3/2010 | Boyan et al. |
| 7,687,462 B2 | 3/2010 | Ting et al. |
| 7,708,741 B1 | 5/2010 | Bonutti |
| 7,713,305 B2 | 5/2010 | Ek |
| 7,722,676 B2 | 5/2010 | Hanson et al. |
| 7,731,720 B2 | 6/2010 | Sand et al. |
| 7,731,738 B2 | 6/2010 | Jackson et al. |
| 7,738,187 B2 | 6/2010 | Pazidis et al. |
| 7,758,643 B2 | 7/2010 | Stone et al. |
| 7,806,872 B2 | 10/2010 | Ponzi |
| 7,815,645 B2 | 10/2010 | Haines |
| 7,828,853 B2 | 11/2010 | Ek et al. |
| 7,842,042 B2 | 11/2010 | Reay-Young et al. |
| 7,857,817 B2 | 12/2010 | Tallarida et al. |
| 7,896,883 B2 | 3/2011 | Ek et al. |
| 7,896,885 B2 | 3/2011 | Miniaci et al. |
| 7,901,408 B2 | 3/2011 | Ek et al. |
| 7,914,545 B2 | 3/2011 | Ek |
| 7,931,683 B2 | 4/2011 | Weber et al. |
| 7,951,163 B2 | 5/2011 | Ek |
| 7,955,382 B2 | 6/2011 | Flanagan et al. |
| 7,959,636 B2 | 6/2011 | Schmieding |
| 7,959,681 B2 | 6/2011 | Lavi |
| 7,967,823 B2 | 6/2011 | Ammann et al. |
| 7,993,360 B2 | 8/2011 | Hacker et al. |
| 7,993,369 B2 | 8/2011 | Dreyfuss |
| 7,998,206 B2 | 8/2011 | Shepard |
| 8,012,206 B2 | 9/2011 | Schmieding |
| 8,021,367 B2 | 9/2011 | Bourke et al. |
| 8,038,652 B2 | 10/2011 | Morrison et al. |
| 8,038,678 B2 | 10/2011 | Schmieding et al. |
| 8,043,315 B2 | 10/2011 | Shepard |
| 8,043,319 B2 | 10/2011 | Lyon et al. |
| 8,048,079 B2 | 11/2011 | Iannarone |
| 8,048,157 B2 | 11/2011 | Albertorio |
| 8,057,478 B2 | 11/2011 | Kuczynski et al. |
| 8,062,301 B2 | 11/2011 | Ammann et al. |
| 8,062,319 B2 | 11/2011 | O'Quinn et al. |
| 8,083,746 B2 | 12/2011 | Novak |
| 8,083,749 B2 | 12/2011 | Taber |
| 8,083,803 B2 | 12/2011 | Albertorio et al. |
| 8,097,040 B2 | 1/2012 | Russo et al. |
| 8,137,406 B2 | 3/2012 | Novak et al. |
| 8,142,502 B2 | 3/2012 | Stone et al. |
| 8,147,559 B2 | 4/2012 | Tallarida et al. |
| 8,152,847 B2 | 4/2012 | Strzepa et al. |
| 8,162,947 B2 | 4/2012 | Dreyfuss |
| 8,167,951 B2 | 5/2012 | Ammann et al. |
| 8,177,738 B2 | 5/2012 | Schmieding et al. |
| 8,177,841 B2 * | 5/2012 | Ek .............................. 623/14.12 |
| 8,182,489 B2 | 5/2012 | Horacek |
| 8,202,282 B2 | 6/2012 | Schmieding et al. |
| 8,202,296 B2 | 6/2012 | Burkhart |
| 8,202,297 B2 | 6/2012 | Burkhart |
| 8,202,298 B2 | 6/2012 | Cook et al. |
| 8,202,306 B2 | 6/2012 | Dreyfuss |
| 8,202,318 B2 | 6/2012 | Willobee |
| 8,211,112 B2 | 7/2012 | Novak et al. |
| 8,221,455 B2 | 7/2012 | Shurnas et al. |
| 8,231,653 B2 | 7/2012 | Dreyfuss |
| 8,231,674 B2 | 7/2012 | Albertorio et al. |
| 8,236,000 B2 | 8/2012 | Ammann et al. |
| 8,267,977 B2 | 9/2012 | Roth |
| 8,298,247 B2 | 10/2012 | Sterrett et al. |
| 8,298,284 B2 | 10/2012 | Cassani |
| 8,303,830 B2 | 11/2012 | Tong et al. |
| 8,308,662 B2 | 11/2012 | Lo |
| 8,308,732 B2 | 11/2012 | Millett et al. |
| 8,323,347 B2 | 12/2012 | Guederian et al. |
| 8,328,716 B2 | 12/2012 | Schmieding et al. |
| 8,333,774 B2 | 12/2012 | Morrison |
| 8,343,186 B2 | 1/2013 | Dreyfuss et al. |
| 8,348,960 B2 | 1/2013 | Michel et al. |
| 8,348,975 B2 | 1/2013 | Dreyfuss |
| 8,353,915 B2 | 1/2013 | Helenbolt et al. |
| 8,361,159 B2 | 1/2013 | Ek |
| 8,377,068 B2 | 2/2013 | Aker et al. |
| 8,382,789 B2 | 2/2013 | Weber et al. |
| 8,382,810 B2 | 2/2013 | Peterson et al. |
| 8,388,624 B2 | 3/2013 | Ek et al. |
| 8,398,678 B2 | 3/2013 | Baker et al. |
| 8,409,209 B2 | 4/2013 | Ammann et al. |
| 8,409,250 B2 | 4/2013 | Schmieding et al. |
| 8,419,794 B2 | 4/2013 | Elattrache et al. |
| 8,425,554 B2 | 4/2013 | Denove et al. |
| 8,430,909 B2 | 4/2013 | Dreyfuss |
| 8,435,272 B2 | 5/2013 | Dougherty et al. |
| 8,439,976 B2 | 5/2013 | Albertorio et al. |
| 8,444,680 B2 | 5/2013 | Dooney, Jr. et al. |
| 8,460,317 B2 | 6/2013 | Merves |
| 8,460,318 B2 | 6/2013 | Murray et al. |
| 8,460,350 B2 | 6/2013 | Albertorio et al. |
| 8,460,379 B2 | 6/2013 | Albertorio et al. |
| 8,475,536 B2 | 7/2013 | Tong et al. |
| 8,486,072 B2 | 7/2013 | Haininger |
| 8,496,662 B2 | 7/2013 | Novak et al. |
| 8,506,573 B2 | 8/2013 | Dreyfuss et al. |
| 8,512,376 B2 | 8/2013 | Thornes |
| 8,512,411 B2 | 8/2013 | Sluss et al. |
| 8,523,872 B2 | 9/2013 | Ek |
| 8,535,330 B2 | 9/2013 | Sherman et al. |
| 8,535,703 B2 | 9/2013 | Schmieding et al. |
| 8,540,717 B2 | 9/2013 | Tallarida et al. |
| 8,540,777 B2 | 9/2013 | Ammann et al. |
| 8,551,101 B2 | 10/2013 | Kuczynski |
| 8,579,940 B2 | 11/2013 | Dreyfuss et al. |
| 8,579,944 B2 | 11/2013 | Holloway et al. |
| 8,591,514 B2 | 11/2013 | Sherman |
| 8,591,523 B2 | 11/2013 | Weber |
| 8,591,544 B2 | 11/2013 | Jolly et al. |
| 8,591,578 B2 | 11/2013 | Albertorio et al. |
| 8,591,592 B2 | 11/2013 | Dreyfuss |
| 8,623,052 B2 | 1/2014 | Dreyfuss et al. |
| 8,628,573 B2 | 1/2014 | Roller et al. |
| 8,652,139 B2 | 2/2014 | Sterrett et al. |
| 8,663,230 B2 | 3/2014 | Miniaci et al. |
| 8,663,250 B2 | 3/2014 | Weber |
| 8,663,251 B2 | 3/2014 | Burkhart et al. |
| 8,663,279 B2 | 3/2014 | Burkhart et al. |
| 8,663,324 B2 | 3/2014 | Schmieding et al. |
| 8,663,333 B2 | 3/2014 | Metcalfe et al. |
| 8,668,738 B2 | 3/2014 | Schmieding et al. |
| 8,702,715 B2 | 4/2014 | Ammann et al. |
| 8,702,752 B2 | 4/2014 | Schmieding et al. |
| 8,709,052 B2 | 4/2014 | Ammann et al. |
| 8,728,131 B2 | 5/2014 | Di Giacomo et al. |
| 8,734,449 B2 | 5/2014 | Schmied et al. |
| 8,753,375 B2 | 6/2014 | Albertorio |
| 8,758,356 B2 | 6/2014 | Fearon et al. |
| 8,764,797 B2 | 7/2014 | Dreyfuss et al. |
| 8,764,807 B2 | 7/2014 | Michel et al. |
| 8,771,279 B2 | 7/2014 | Philippon et al. |
| 8,771,351 B2 | 7/2014 | ElAttrache et al. |
| 2001/0010023 A1 | 7/2001 | Schwartz et al. |
| 2001/0012967 A1 | 8/2001 | Mosseri |
| 2001/0034526 A1 | 10/2001 | Kuslich et al. |
| 2001/0039455 A1 | 11/2001 | Simon et al. |
| 2001/0053914 A1 | 12/2001 | Landry et al. |
| 2001/0056266 A1 | 12/2001 | Tallarida et al. |
| 2002/0022847 A1 | 2/2002 | Ray, III et al. |
| 2002/0022889 A1 | 2/2002 | Chibrac et al. |
| 2002/0049444 A1 | 4/2002 | Knox |
| 2002/0055783 A1 | 5/2002 | Tallarida et al. |
| 2002/0106393 A1 | 8/2002 | Bianchi et al. |
| 2002/0138150 A1 | 9/2002 | Leclercq |
| 2002/0143342 A1 | 10/2002 | Hangody et al. |
| 2002/0147498 A1 | 10/2002 | Tallarida et al. |
| 2002/0155144 A1 | 10/2002 | Troczynski et al. |
| 2002/0156480 A1 | 10/2002 | Overes et al. |
| 2002/0173797 A1 | 11/2002 | Van Zile et al. |
| 2003/0028196 A1 | 2/2003 | Bonutti |
| 2003/0060887 A1 | 3/2003 | Ek |
| 2003/0065391 A1 | 4/2003 | Re et al. |
| 2003/0100953 A1 | 5/2003 | Rosa et al. |

(56) References Cited

U.S. PATENT DOCUMENTS

| | | |
|---|---|---|
| 2003/0105465 A1 | 6/2003 | Schmieding et al. |
| 2003/0120276 A1 | 6/2003 | Tallarida et al. |
| 2003/0120278 A1 | 6/2003 | Morgan et al. |
| 2003/0130741 A1 | 7/2003 | McMinn |
| 2003/0144736 A1 | 7/2003 | Sennett |
| 2003/0171756 A1 | 9/2003 | Fallin et al. |
| 2003/0181878 A1 | 9/2003 | Tallarida et al. |
| 2003/0195470 A1 | 10/2003 | Ponzi |
| 2003/0204195 A1 | 10/2003 | Keane et al. |
| 2003/0204267 A1 | 10/2003 | Hazebrouck et al. |
| 2003/0216669 A1 | 11/2003 | Lang et al. |
| 2003/0216742 A1 | 11/2003 | Wetzler et al. |
| 2003/0225456 A1 | 12/2003 | Ek |
| 2003/0225457 A1 | 12/2003 | Justin et al. |
| 2003/0229352 A1 | 12/2003 | Penenberg |
| 2004/0015170 A1 | 1/2004 | Tallarida et al. |
| 2004/0033212 A1 | 2/2004 | Thomson et al. |
| 2004/0034359 A1 | 2/2004 | Schmieding et al. |
| 2004/0034437 A1 | 2/2004 | Schmieding |
| 2004/0039389 A1 | 2/2004 | West, Jr. et al. |
| 2004/0082906 A1 | 4/2004 | Tallarida et al. |
| 2004/0092946 A1 | 5/2004 | Bagga et al. |
| 2004/0106928 A1 | 6/2004 | Ek |
| 2004/0133276 A1 | 7/2004 | Lang et al. |
| 2004/0138754 A1 | 7/2004 | Lang et al. |
| 2004/0138758 A1 | 7/2004 | Evans et al. |
| 2004/0148030 A1 | 7/2004 | Ek |
| 2004/0153087 A1 | 8/2004 | Sanford et al. |
| 2004/0167632 A1 | 8/2004 | Wen et al. |
| 2004/0167633 A1 | 8/2004 | Wen et al. |
| 2004/0176775 A1 | 9/2004 | Burkus et al. |
| 2004/0193172 A1 | 9/2004 | Ross et al. |
| 2004/0193267 A1 | 9/2004 | Jones et al. |
| 2004/0193268 A1 | 9/2004 | Hazebrouck |
| 2004/0193281 A1 | 9/2004 | Grimes |
| 2004/0199166 A1 | 10/2004 | Schmieding et al. |
| 2004/0204760 A1 | 10/2004 | Fitz et al. |
| 2004/0210309 A1 | 10/2004 | Denzer et al. |
| 2004/0220574 A1 | 11/2004 | Pelo et al. |
| 2004/0230315 A1 | 11/2004 | Ek |
| 2004/0260303 A1 | 12/2004 | Carrison |
| 2005/0015153 A1 | 1/2005 | Goble et al. |
| 2005/0038520 A1 | 2/2005 | Binette et al. |
| 2005/0043805 A1 | 2/2005 | Chudik |
| 2005/0043808 A1 | 2/2005 | Felt et al. |
| 2005/0065612 A1 | 3/2005 | Winslow |
| 2005/0075642 A1 | 4/2005 | Felt |
| 2005/0143731 A1 | 6/2005 | Justin et al. |
| 2005/0143745 A1 | 6/2005 | Hodorek et al. |
| 2005/0143831 A1 | 6/2005 | Justin et al. |
| 2005/0149044 A1 | 7/2005 | Justin et al. |
| 2005/0154398 A1 | 7/2005 | Miniaci et al. |
| 2005/0177171 A1 | 8/2005 | Wetzler et al. |
| 2005/0209705 A1 | 9/2005 | Niederauer et al. |
| 2005/0222687 A1 | 10/2005 | Vunjak-Novakovic et al. |
| 2005/0229323 A1 | 10/2005 | Mills et al. |
| 2005/0251268 A1 | 11/2005 | Truncale |
| 2005/0287187 A1 | 12/2005 | Mansmann |
| 2006/0004461 A1 | 1/2006 | Justin et al. |
| 2006/0009774 A1 | 1/2006 | Goble et al. |
| 2006/0020343 A1 | 1/2006 | Ek |
| 2006/0052878 A1 | 3/2006 | Schmieding |
| 2006/0058744 A1 | 3/2006 | Tallarida et al. |
| 2006/0058809 A1 | 3/2006 | Zink et al. |
| 2006/0058883 A1 | 3/2006 | Aram et al. |
| 2006/0069394 A1 | 3/2006 | Weiler et al. |
| 2006/0074430 A1 | 4/2006 | Deffenbaugh et al. |
| 2006/0085006 A1 | 4/2006 | Ek |
| 2006/0085077 A1 | 4/2006 | Cook et al. |
| 2006/0142772 A1 | 6/2006 | Ralph et al. |
| 2006/0149370 A1 | 7/2006 | Schmieding et al. |
| 2006/0167560 A1 | 7/2006 | Heck et al. |
| 2006/0184187 A1 | 8/2006 | Surti |
| 2006/0190002 A1 | 8/2006 | Tallarida |
| 2006/0195112 A1 | 8/2006 | Ek |
| 2006/0217728 A1 | 9/2006 | Chervitz et al. |
| 2006/0229726 A1 | 10/2006 | Ek |
| 2006/0271059 A1 | 11/2006 | Reay-Young et al. |
| 2007/0005143 A1 | 1/2007 | Ek |
| 2007/0038302 A1 | 2/2007 | Shultz et al. |
| 2007/0038307 A1 | 2/2007 | Webster et al. |
| 2007/0073394 A1 | 3/2007 | Seedhom et al. |
| 2007/0093842 A1 | 4/2007 | Schmieding |
| 2007/0093848 A1 | 4/2007 | Harris et al. |
| 2007/0093890 A1 | 4/2007 | Eliasen et al. |
| 2007/0093896 A1 | 4/2007 | Malinin |
| 2007/0118136 A1 | 5/2007 | Ek |
| 2007/0118224 A1 | 5/2007 | Shah et al. |
| 2007/0123921 A1 | 5/2007 | Ek |
| 2007/0134291 A1 | 6/2007 | Ting et al. |
| 2007/0173850 A1 | 7/2007 | Rangaiah et al. |
| 2007/0179608 A1 | 8/2007 | Ek |
| 2007/0233128 A1 | 10/2007 | Schmieding et al. |
| 2007/0244484 A1 | 10/2007 | Luginbuehl |
| 2007/0250067 A1 | 10/2007 | Schmieding et al. |
| 2007/0255399 A1 | 11/2007 | Eliasen et al. |
| 2007/0255412 A1 | 11/2007 | Hajaj et al. |
| 2007/0265700 A1 | 11/2007 | Eliasen et al. |
| 2007/0270873 A1 | 11/2007 | Flickinger et al. |
| 2007/0282455 A1 | 12/2007 | Luginbuehl et al. |
| 2007/0288031 A1 | 12/2007 | Dreyfuss et al. |
| 2007/0299519 A1 | 12/2007 | Schmieding |
| 2008/0004659 A1 | 1/2008 | Burkhart et al. |
| 2008/0015709 A1 | 1/2008 | Evans et al. |
| 2008/0027430 A1 | 1/2008 | Montgomery et al. |
| 2008/0033443 A1 | 2/2008 | Sikora et al. |
| 2008/0033447 A1 | 2/2008 | Sand |
| 2008/0046084 A1 | 2/2008 | Sledge |
| 2008/0086139 A1 | 4/2008 | Bourke et al. |
| 2008/0097618 A1 | 4/2008 | Baker et al. |
| 2008/0103506 A1 | 5/2008 | Volpi et al. |
| 2008/0154271 A1 | 6/2008 | Berberich et al. |
| 2008/0172125 A1 | 7/2008 | Ek |
| 2008/0183290 A1 | 7/2008 | Baird et al. |
| 2008/0188935 A1 | 8/2008 | Saylor et al. |
| 2008/0195113 A1 | 8/2008 | Sikora |
| 2008/0208201 A1 | 8/2008 | Moindreau et al. |
| 2008/0262625 A1 | 10/2008 | Spriano et al. |
| 2008/0275512 A1 | 11/2008 | Albertorio et al. |
| 2008/0294168 A1 | 11/2008 | Wieland |
| 2008/0306483 A1 | 12/2008 | Iannarone |
| 2008/0317807 A1 | 12/2008 | Lu et al. |
| 2009/0018543 A1 | 1/2009 | Ammann et al. |
| 2009/0054899 A1 | 2/2009 | Ammann et al. |
| 2009/0069816 A1 | 3/2009 | Sasing et al. |
| 2009/0076512 A1 | 3/2009 | Ammann et al. |
| 2009/0112211 A1 | 4/2009 | Johnstone |
| 2009/0138077 A1 | 5/2009 | Weber et al. |
| 2009/0143783 A1 | 6/2009 | Dower |
| 2009/0143784 A1 | 6/2009 | Petersen et al. |
| 2009/0149860 A1 | 6/2009 | Scribner et al. |
| 2009/0198288 A1 | 8/2009 | Hoof et al. |
| 2009/0210057 A1 | 8/2009 | Liao et al. |
| 2009/0216268 A1 | 8/2009 | Panter |
| 2009/0216285 A1 | 8/2009 | Ek et al. |
| 2009/0222012 A1 | 9/2009 | Karnes et al. |
| 2009/0228105 A1 | 9/2009 | Son et al. |
| 2009/0234452 A1 | 9/2009 | Steiner et al. |
| 2009/0264889 A1 | 10/2009 | Long et al. |
| 2009/0264928 A1 | 10/2009 | Blain |
| 2009/0275950 A1 | 11/2009 | Sterrett et al. |
| 2009/0276052 A1 | 11/2009 | Regala et al. |
| 2010/0003638 A1 | 1/2010 | Collins et al. |
| 2010/0015244 A1 | 1/2010 | Jain et al. |
| 2010/0028387 A1 | 2/2010 | Balasundaram et al. |
| 2010/0028999 A1 | 2/2010 | Nain |
| 2010/0036381 A1 | 2/2010 | Vanleeuwen et al. |
| 2010/0092535 A1 | 4/2010 | Cook et al. |
| 2010/0112519 A1 | 5/2010 | Hall et al. |
| 2010/0168854 A1 | 7/2010 | Luers et al. |
| 2010/0249930 A1 | 9/2010 | Myers |
| 2010/0256645 A1 | 10/2010 | Zajac et al. |
| 2010/0256758 A1 | 10/2010 | Gordon et al. |
| 2010/0268227 A1 | 10/2010 | Tong et al. |

(56) References Cited

U.S. PATENT DOCUMENTS

| | | |
|---|---|---|
| 2010/0268330 A1 | 10/2010 | Tong et al. |
| 2010/0268346 A1 | 10/2010 | Tong et al. |
| 2010/0268347 A1 | 10/2010 | Tong et al. |
| 2011/0009964 A1 | 1/2011 | Schwartz et al. |
| 2011/0059312 A1 | 3/2011 | Howling et al. |
| 2011/0066242 A1 | 3/2011 | Lu et al. |
| 2011/0106271 A1 | 5/2011 | Regala et al. |
| 2011/0125263 A1 | 5/2011 | Webster et al. |
| 2011/0152869 A1 | 6/2011 | Ek et al. |
| 2011/0190902 A1 | 8/2011 | Tong et al. |
| 2011/0196367 A1 | 8/2011 | Gallo |
| 2011/0213375 A1 | 9/2011 | Sikora et al. |
| 2011/0238069 A1 | 9/2011 | Zajac et al. |
| 2011/0251621 A1 | 10/2011 | Sluss et al. |
| 2011/0257753 A1 | 10/2011 | Gordon et al. |
| 2011/0300186 A1 | 12/2011 | Hellstrom et al. |
| 2011/0301716 A1 | 12/2011 | Sirivisoot et al. |
| 2012/0022656 A1 | 1/2012 | Lavi |
| 2012/0027837 A1 | 2/2012 | DeMuth et al. |
| 2012/0051489 A1 | 3/2012 | Varanasi et al. |
| 2012/0109136 A1 | 5/2012 | Bourque et al. |
| 2012/0116502 A1 | 5/2012 | Su et al. |
| 2012/0123474 A1 | 5/2012 | Zajac et al. |
| 2012/0123541 A1 | 5/2012 | Albertorio et al. |
| 2012/0150225 A1 | 6/2012 | Burkhart et al. |
| 2012/0150286 A1 | 6/2012 | Weber et al. |
| 2012/0165868 A1 | 6/2012 | Burkhart et al. |
| 2012/0183799 A1 | 7/2012 | Steele et al. |
| 2012/0185058 A1 | 7/2012 | Albertorio et al. |
| 2012/0189833 A1 | 7/2012 | Suchanek et al. |
| 2012/0189844 A1 | 7/2012 | Jain et al. |
| 2012/0209278 A1 | 8/2012 | Ries et al. |
| 2012/0265298 A1 | 10/2012 | Schmieding et al. |
| 2013/0023907 A1 | 1/2013 | Sterrett et al. |
| 2013/0023927 A1 | 1/2013 | Cassani |
| 2013/0046312 A1 | 2/2013 | Millett et al. |
| 2013/0096563 A1 | 4/2013 | Meade et al. |
| 2013/0096612 A1 | 4/2013 | Zajac et al. |
| 2013/0103104 A1 | 4/2013 | Krupp et al. |
| 2013/0110165 A1 | 5/2013 | Burkhart et al. |
| 2013/0138108 A1 | 5/2013 | Dreyfuss et al. |
| 2013/0138150 A1 | 5/2013 | Baker et al. |
| 2013/0150885 A1 | 6/2013 | Dreyfuss |
| 2013/0165954 A1 | 6/2013 | Dreyfuss et al. |
| 2013/0165972 A1 | 6/2013 | Sullivan |
| 2013/0178871 A1 | 7/2013 | Koogle, Jr. et al. |
| 2013/0184818 A1 | 7/2013 | Coughlin et al. |
| 2013/0190885 A1 | 7/2013 | Ammann et al. |
| 2013/0204257 A1 | 8/2013 | Zajac |
| 2013/0204259 A1 | 8/2013 | Zajac |
| 2013/0205936 A1 | 8/2013 | Schmieding et al. |
| 2013/0218176 A1 | 8/2013 | Denove et al. |
| 2013/0238099 A1 | 9/2013 | Hardy et al. |
| 2013/0245775 A1 | 9/2013 | Metcalfe |
| 2013/0268073 A1 | 10/2013 | Albertorio et al. |
| 2013/0304209 A1 | 11/2013 | Schmieding et al. |
| 2013/0331886 A1 | 12/2013 | Thornes |
| 2013/0338792 A1 | 12/2013 | Schmieding et al. |
| 2013/0345747 A1 | 12/2013 | Dreyfuss |
| 2013/0345748 A1 | 12/2013 | Dreyfuss |
| 2014/0012267 A1 | 1/2014 | Skiora et al. |
| 2014/0012389 A1 | 1/2014 | Ek |
| 2014/0052178 A1 | 2/2014 | Dooney, Jr. |
| 2014/0052179 A1 | 2/2014 | Dreyfuss et al. |
| 2014/0074164 A1 | 3/2014 | Dreyfuss et al. |
| 2014/0074239 A1 | 3/2014 | Albertorio et al. |
| 2014/0081273 A1 | 3/2014 | Sherman |
| 2014/0081399 A1 | 3/2014 | Roller et al. |
| 2014/0088601 A1 | 3/2014 | Kuczynski |
| 2014/0088602 A1 | 3/2014 | Ammann et al. |
| 2014/0114322 A1 | 4/2014 | Perez, III |
| 2014/0114367 A1 | 4/2014 | Jolly et al. |
| 2014/0121700 A1 | 5/2014 | Dreyfuss et al. |
| 2014/0121701 A1 | 5/2014 | Dreyfuss et al. |
| 2014/0128889 A1 | 5/2014 | Sullivan et al. |
| 2014/0128915 A1 | 5/2014 | Dreyfuss et al. |
| 2014/0128921 A1 | 5/2014 | Parsons et al. |
| 2014/0155902 A1 | 6/2014 | Sikora et al. |
| 2014/0188232 A1 | 7/2014 | Metcalfe et al. |
| 2014/0194880 A1 | 7/2014 | Schmieding et al. |

FOREIGN PATENT DOCUMENTS

| | | |
|---|---|---|
| AU | 2002248198 B2 | 5/2007 |
| AU | 2005202099 B2 | 6/2007 |
| AU | 2002357284 B2 | 8/2007 |
| AU | 2006202337 B2 | 5/2008 |
| AU | 2003262428 | 8/2009 |
| AU | 2007216648 B2 | 11/2009 |
| AU | 2004216106 B2 | 6/2010 |
| AU | 2008207536 B2 | 3/2011 |
| CA | 2470194 C | 2/2011 |
| DE | 2933174 | 4/1980 |
| DE | 3516743 | 11/1986 |
| DE | 3840466 | 6/1990 |
| DE | 19505083 | 11/1995 |
| EP | 0241240 | 10/1987 |
| EP | 0350780 | 1/1990 |
| EP | 0485678 | 5/1992 |
| EP | 0327387 | 9/1992 |
| EP | 0505634 | 9/1992 |
| EP | 0736292 | 10/1996 |
| EP | 0903125 | 3/1999 |
| EP | 0903127 | 3/1999 |
| EP | 0993812 | 4/2000 |
| EP | 0661023 | 8/2001 |
| EP | 1426013 | 9/2004 |
| EP | 1278460 | 4/2009 |
| EP | 2314257 | 2/2013 |
| FR | 2242068 | 3/1975 |
| FR | 2642301 | 3/1990 |
| FR | 2676917 | 12/1992 |
| FR | 2693650 | 1/1994 |
| FR | 2718014 | 10/1995 |
| FR | 2733904 | 11/1996 |
| FR | 2739151 | 3/1997 |
| GB | 2281577 | 3/1995 |
| GB | 2372707 | 9/2002 |
| JP | 61502029 | 9/1986 |
| JP | 63300758 | 12/1988 |
| JP | 3504932 | 10/1991 |
| JP | H03-092328 | 11/1992 |
| JP | 518511 | 3/1993 |
| JP | 06339490 | 12/1994 |
| JP | 11244315 | 9/1999 |
| JP | 2001525210 | 12/2001 |
| JP | 2002291779 | 10/2002 |
| JP | 2003554096 | 11/2003 |
| WO | 8803781 | 6/1988 |
| WO | 8909578 | 10/1989 |
| WO | 9409730 | 5/1994 |
| WO | 9427507 | 12/1994 |
| WO | 9624304 | 8/1996 |
| WO | 9722306 | 6/1997 |
| WO | 9920192 | 4/1999 |
| WO | 0013597 | 3/2000 |
| WO | 0105336 | 1/2001 |
| WO | 0166021 | 9/2001 |
| WO | 0166022 | 9/2001 |
| WO | 0182677 | 11/2001 |
| WO | 0191648 | 12/2001 |
| WO | 0191672 | 12/2001 |
| WO | 0217821 | 3/2002 |
| WO | 02086180 | 10/2002 |
| WO | 03047470 | 6/2003 |
| WO | 03051210 | 6/2003 |
| WO | 03051211 | 6/2003 |
| WO | 03061516 | 7/2003 |
| WO | 03065909 | 8/2003 |
| WO | 2004014261 | 2/2004 |
| WO | 2004026170 | 4/2004 |
| WO | 2004052216 | 6/2004 |
| WO | 2004075777 | 9/2004 |
| WO | 2005051231 | 6/2005 |

(56) References Cited

FOREIGN PATENT DOCUMENTS

| WO | 2006004885 | 1/2006 |
|---|---|---|
| WO | 2006091686 | 8/2006 |
| WO | 2014008126 | 1/2014 |

OTHER PUBLICATIONS

Notice of Allowance issued in corresponding U.S. Appl. No. 10/308,718 dated Sep. 11, 2006.
Office Action issued in corresponding U.S. Appl. No. 11/326,133 dated Oct. 17, 2007.
United States Office Action issued is related U.S. Appl. No. 10/760,965 dated Feb. 19, 2008.
Australian Office Action issued in related Australian Patent Application No. 2004293042 dated Feb. 20, 2008.
Australian Office Action issued in related Australian Patent Application No. 2003262428 dated Mar. 20, 2008.
U.S. Office Action issued in related U.S. Appl. No. 11/326,133 dated Jun. 12, 2008.
International Search Report and Written Opinion dated Jun. 24, 2008 issued in related International Patent Application No. PCT/US07/73685.
International Search Report and Written Opinion dated Jun. 11, 2008 issued in related International Patent Application No. PCT/US07/25284.
International Search Report and Written Opinion dated Aug. 8, 2008 issued in related International Patent Application No. PCT/US08/53988.
U.S. Office Action issued in related U.S. Appl. No. 10/99,453 dated Jun. 5, 2007.
Japanese Office Action dated Jul. 22, 2008 issued in related Japanese Patent Application No. 2006-501193.
U.S. Office Action issued in related U.S. Appl. No. 10/373,463 dated Apr. 21, 2008.
Notice of Allowance received in U.S. Appl. No. 10/618,887 dated Aug. 15, 2008.
Australia Office Action issued in related Australian Patent Application No. 2007216648 dated May 30, 2008.
European Office Action issued in related European Patent Application No. 01932833.5-2310 dated Apr. 25, 2008.
U.S. Office Action received in related U.S. Appl. No. 11/169,326 dated Jun. 30, 2008.
U.S. Office Action received in related U.S. Appl. No. 11/169,326 dated Jul. 27, 2007.
U.S. Office Action received in related U.S. Appl. No. 11/169,326 dated Apr. 17, 2007.
U.S. Office Action received in related U.S. Appl. No. 11/169,326 dated Mar. 9, 2007.
Canadian Office Action issued in related Canadian Patent Application No. 2546582 dated Aug. 21, 2008.
U.S. Office Action issued in related U.S. Appl. No. 10/994,453 dated Sep. 3, 2008.
U.S. Office Action dated Oct. 21, 2008 issued in related U.S. Appl. No. 11/461,240.
U.S. Office Action dated Jun. 25, 2008 issued in related U.S. Appl. No. 11/359,891.
U.S. Office Action dated Sep. 25, 2008 issued in related U.S. Appl. No. 11/326,133.
U.S. Office Action dated Jul. 2, 2008 issued in related U.S. Appl. No. 11/379,151.
European Office Action dated Oct. 6, 2008 issued in related European Patent Application No. 01932833.5-2310.
U.S. Office Action dated Jun. 27, 2008 issued in related U.S. Appl. No. 10/760,965.
International Search Report and Written Opinion dated Oct. 1, 2008 issued in related International Patent Application No. PCT/US08/53194.
International Search Report and Written Opinion dated Oct. 9, 2008 issued in related International Patent Application No. PCT/US07/82262.

European Search Report dated Nov. 4, 2008 issued in related European Patent Application No. 04811836.8-2310.
Habermeyer, "Eclipse, Schaftfreie Schulterprothese Operationsanleitung," (dated unknown).
U.S. Office Action dated Jan. 9, 2009 issued in related U.S. Appl. No. 10/373,463.
Canadian Office Action dated Dec. 9, 2008 issued in related Canadian Patent Application No. 2407440.
Supplemental European Search Report dated Nov. 6, 2008 issued in related European Patent Application No. 05791453.3-2310.
Japanese Office Action dated Dec. 19, 2008 issued in Japanese Patent Application No. 2006501193.
Japanese Office Action dated Jan. 13, 2009 issued in Japanese Patent Application No. 2003552147.
International Search Report dated Jan. 30, 2006 issued in related International Patent Application No. PCT/US04/39181.
U.S. Office Action dated Mar. 27, 2009 issued in related U.S. Appl. No. 11/169,326.
European Office Action dated Feb. 26, 2009 in related European Patent Application No. 05791453.3.
McCarty, III., et al., "Nonarthoplasty Treatment of Glenohumeral Cartilage Lesions," Arthroscopy, The Journal of Arthroscopic and related Surgery, vol. 21, No. 9; Sep. 2005 (pp. 1131-1142).
Bushnell, et al., "Bony Instability of the Shoulder," Arthroscopy, The Journal of Arthroscopic and related Surgery, vol. 24, No. 9; Sep. 2005 (pp. 1061-1073).
Scalise, et al., "Resurfacing Arthroplasty of the Humerus: Indications, Surgical Technique, and Clinical Results," Techniques in Shoulder and Elbow Surgery 8(3):152-160; 2007.
Davidson, et al., "Focal Anatomic Patellofemoral Inlay Resurfacing: Theoretic Basis, Surgical Technique, and Case Reports," Orthop. Clin. N. Am., 39 (2008) pp. 337-346.
Provencher, et al., "Patellofemoral Kinematics After Limited Resurfacing of the Trochlea," The Journal of Knee Surgery, vol. 22 No. 2 (2008) pp. 1-7.
Dawson, et al., "The Management of Localized Articular Cartilage Lesions of the Humeral Head in the Athlete," Operative Techniques in Sports Medicine, vol. 16, Issue 1, pp. 14-20 (2008).
Uribe, et al., "Partial Humeral Head Resurfacing for Osteonecrosis," Journal of Shoulder and Elbow Surgery, (2009) 6 pages.
Burks, "Implant Arthroplasty of the First Metatarsalphalangeal Joint," Clin. Podiatr. Med. Surg., 23 (2006) pp. 725-731.
Hasselman, et al., "Resurfacing of the First Metatarsal Head in the Treatment of Hallux Rigidus," Techniques in Foot & Ankle Surgery 7(1):31-40, 2008.
Jäger, et al., "Partial hemi-resurfacing of the hip joint—a new approach to treat local osteochondral defects?" Biomed Tech 2006; 51:371-376 (2006).
U.S. Office Action dated May 18, 2010 issued in related U.S. Appl. No. 12/415,503.
Japanese Notice of Reasons for Rejection dated Jun. 1, 2010 issued in related Japanese Patent Application No. 2003394702.
European Office Action dated Jun. 1, 2010 issued in related European Patent Application No. 04811836.8-2310.
Japanese Notice of Reasons for Rejection dated Jun. 29, 2010 issued in related Japanese Patent Application No. 2007519417.
Australian Office Action dated Jun. 11, 2010 issued in related Australian Patent Application No. 2005277078.
International Search Report dated Jun. 9, 2010 issued in related International Patent Application No. PCT/US2010/031594.
European Office Action dated May 7, 2010 issued in related European Patent Application No. 06733631.3-2310.
International Search Report dated Jun. 18, 2010 issued in related International Patent Application No. PCT/US2010/031602.
U.S. Office Action dated Jun. 8, 2010 issued in related U.S. Appl. No. 11/209,170.
Office Action dated Sep. 2, 2010 issued in related U.S. Appl. No. 12/415,503.
Office Action dated Aug. 30, 2010 issued in related U.S. Appl. No. 12/397,095.
Office Action dated Jul. 21, 2010 issued in related U.S. Appl. No. 11/551,912.

(56) References Cited

OTHER PUBLICATIONS

Office Action dated Aug. 5, 2010 issued in related U.S. Appl. No. 11/325,133.
Notice of Allowance dated Aug. 6, 2010 issued in related U.S. Appl. No. 11/359,892.
Canadian Office Action dated Jul. 29, 2010 issued in related Canadian Patent Application No. 2470936.
Supplemental European Search Report dated Aug. 9, 2010 issued in related European Patent Application No. 04714211.2-2300.
Australian Office Action dated Aug. 23, 2010 issued in related Australian Patent Application No. 2006203909.
Notice of Allowance dated Sep. 9, 2010 issued in related U.S. Appl. No. 10/994,453.
Office Action dated Sep. 21, 2010 issued in related U.S. Appl. No. 11/169,326.
Office Action dated Sep. 29, 2010 issued in related U.S. Appl. No. 11/461,240.
Office Action dated Oct. 11, 2010 issued in related Australian Patent Application No. 2006216725.
International Preliminary Report on Patentability dated Sep. 16, 2010 issued in related International Patent Application No. PCT/US2009/035889.
Supplemental Notice of Allowance dated Oct. 13, 2010 issued in related U.S. Appl. No. 10/994,453.
Supplemental Notice of Allowance dated Oct. 6, 2010 issued in related U.S. Appl. No. 12/415,503.
U.S. Office Action dated Oct. 15, 2010 received in related U.S. Appl. No. 12/027,121.
U.S. Supplemental Notice of Allowance dated Oct. 28, 2010 issued in related U.S. Appl. No. 12/415,503.
European Search Report dated Nov. 4, 2010 issued in related European Patent Application No. 07862736.1-1269.
Notice of Allowance dated Nov. 26, 2010 issued in related U.S. Appl. No. 11/209,170.
Supplemental Notice of Allowance dated Dec. 8, 2010 issued in related U.S. Appl. No. 11/209,170.
Notice of Allowance dated Dec. 13, 2010 issued in related U.S. Appl. No. 12/397,095.
Notice of Allowance dated Jan. 5, 2011 issued in related U.S. Appl. No. 11/326,133.
Supplemental Notice of Allowance dated Feb. 14, 2011 issued in related U.S. Appl. No. 11/326,133.
Canadian Office Action dated Jan. 7, 2011 issued in related Canadian Patent Application No. 2407440.
European Office Action dated Dec. 23, 2010 issued in related European Patent Application No. 028051882.9-2310.
European Office Action dated Dec. 30, 2010 issued in related European Patent Application No. 01997077.1-2310.
Extended Search Report dated Feb. 22, 2011 issued in European Patent Application No. 10012693.7, 8 pages.
Notice of Allowance dated Mar. 2, 2011 issued in Australian Patent Application No. 2008207536, 3 pages.
Notice of Allowance dated Mar. 15, 2011 issued in U.S. Appl. No. 11/551,912, 7 pages.
U.S. Office Action dated Apr. 11, 2011 issued in U.S. Appl. No. 11/779,044, 10 pages.
Notice of Allowance dated Apr. 28, 2011 issued in U.S. Appl. No. 12/027,121, 9 pages.
U.S. Office Action dated May 11, 2011 issued in U.S. Appl. No. 11/623,513, 12 pages.
U.S. Office Action dated May 11, 2011 issued in U.S. Appl. No. 12/001,473, 18 pages.
U.S. Office Action dated May 16, 2011 issued in U.S. Appl. No. 12/582,345, 9 pages.
International Search Report and Written Opinion dated May 19, 2011 issued in PCT Application No. PCT/US2011/027451, 11 pages.
Canadian Notice of Allowance dated Jun. 1, 2011 issued in Canadian Patent Application No. 2,470,936, 1 page.
Examiner interview summary dated Jul. 1, 2011 issued in European Patent Application No. 02 805 182.9, 3 pages.
U.S. Final Office Action dated Jul. 8, 2011 issued in U.S. Appl. No. 11/169,326, 26 pages.
Ascension Orthopedics, Inc., Ascension Orthopedics Announces Market Release of TITAN™ Inset Mini Glenoid, PR Newswire, downloaded from internet Jul. 18, 2011, http://www.orthospinenews.com/ascension-orthopedics-announces-market-release-of-titan™-inset-mini-glenoid, Jul. 6, 2011, 2 pages.
PCT International Preliminary Report on Patentability dated Sep. 9, 2011 issued in PCT Patent Application No. PCT/US2010/025464, 7 pages.
Sullivan, "Hallux Rigidus: MTP Implant Arthroplasty," Foot Ankle Clin. N. Am. 14 (2009) pp. 33-42.
Cook, et al, "Meta-analysis of First Metatarsophalangeal Joint Implant Arthroplasty," Journal of Foot and Ankle Surgery, vol. 48, Issue 2, pp. 180-190 (2009).
Derner, "Complications and Salvage of Elective Central Metatarsal Osteotomies," Clin. Podiatr. Med. Surg. 26 (2009) 23-35.
Kirker-Head, et al., "Safety of, and Biological Functional Response to, a Novel Metallic Implant for the Management of Focal Full-Thickness Cartilage Defects: Preliminary Assessment in an Animal Model Out to 1 year," Journal of Orthopedic Research, May 2006 pp. 1095-1108.
Becher, et al. "Effects of a contoured articular prosthetic device on tibiofemoral peak contact pressure: a biomechanical study," Knee Surg Sports Traumatol Arthrosc. Jan. 2008; 16(1): 56-63.
United States Office Action dated May 13, 2009 issued in related U.S. Appl. No. 11/359,892.
United States Office Action dated May 18, 2009 issued in related U.S. Appl. No. 11/209,170.
United States Office Action dated May 1, 2009 issued in related U.S. Appl. No. 11/461,240.
Australian Office Action dated Jan. 29, 2009 issued in related Australian Patent Application No. 2004216106.
European Search Report dated Apr. 22, 2009 issued in related European Patent Application No. 09002088.4.
U.S. Office Action dated Aug. 30, 2006 issued in related U.S. Appl. No. 10/618,887.
U.S. Office Action dated Jan. 15, 2008 issued in related U.S. Appl. No. 10/618,887.
U.S. Office Action dated May 28, 2009 issued in related U.S. Appl. No. 11/359,891.
International Search Report and Written Opinion dated Jun. 1, 2009 issued in related International Patent Application No. PCT/US2009/035889.
International Preliminary Report and Patentability dated May 7, 2009 issued in related International Patent Application No. PCT/US2007/082262.
Supplemental European Search Report dated May 28, 2009 issued in related International European Patent Application No. 01997077.1.
Supplemental European Search Report dated May 11, 2009 issued in related International European Patent Application No. 02805182.9.
Notice of Allowance dated Feb. 20, 2009 issued in related U.S. Appl. No. 10/618,887.
Notice of Reasons for Rejection issued in related Japanese Patent Application No. 2003-394702 mailed Jul. 21, 2009.
Notice of Reasons for Rejection issued in related Japanese Patent Application No. 20-541615 mailed May 26, 2009.
International Preliminary Report on Patentability issued in related International Patent Application No. PCT/US2007/025284 dated Jun. 25, 2009.
Office Action issued in related Australian Patent Application No. 2007216648 dated Jul. 28, 2009.
European Search Report dated Jul. 10, 2009 issued in related European Patent Application No. 09002088.4.
International Preliminary Report on Patentability dated Aug. 20, 2009 issued in related International Patent Application No. 2008053194.
Notice of Allowance dated Aug. 25, 2009 issued in related U.S. Appl. No. 11/379,151.
Notice of Allowance dated Aug. 27, 2009 issued in related U.S. Appl. No. 10/760,965.
U.S. Office Action dated Sep. 2, 2009 issued in relation U.S. Appl. No. 10/994,453.

(56) References Cited

OTHER PUBLICATIONS

U.S. Office Action dated Oct. 5, 2009 issued in relation U.S. Appl. No. 10/789,545.
U.S. Office Action dated Oct. 15, 2009 issued in relation U.S. Appl. No. 11/551,912.
U.S. Office Action dated Oct. 14, 2009 issued in relation U.S. Appl. No. 11/461,240.
Australian Notice of Allowance dated Oct. 29, 2009 issued in related Australian Patent Application No. 2007216648.
Notice of Allowance dated Oct. 9, 2009 issued in related U.S. Appl. No. 10/373,463.
Australian Office Action dated Oct. 29, 2009 issued in related Australian Patent Application No. 2007203623.
Japanese Notice of Reasons for Rejection dated Sep. 8, 2009 issued in related Japanese Patent Application No. 2003552147.
Notice of Reasons for Rejection dated Nov. 17, 2009 issued in Japanese Patent Application No. 2007-519417.
European Search Report dated Dec. 3, 2009 issued in related European Patent Application No. 06735827.5.
Office Action dated Dec. 24, 2009 issued in related U.S. Appl. No. 10/994,453.
Supplemental Notice of Allowance dated Nov. 25, 2009 issued in related U.S. Appl. No. 10/373,463.
European Office Action dated Jan. 11, 2010 issued in related European Patent Application No. 2005218302.
U.S. Office Action dated Jan. 25, 2010 issued in related U.S. Appl. No. 11/326,133.
Australian Office Action dated Apr. 9, 2010 issued in related Australian Patent Application No. 2005260590.
U.S. Office Action dated Mar. 2, 2010 issued in related U.S. Appl. No. 11/169,326.
U.S. Office Action dated Mar. 9, 2010 issued in related U.S. Appl. No. 11/359,892.
Australian Office Action dated Feb. 26, 2010 issued in related Australian Patent Application No. 2008207536.
Supplemental Notice of Allowance dated Feb. 2, 2010 issued in related U.S. Appl. No. 10/373,463.
European office communication dated Feb. 10, 2010 issued in European Patent Application No. 09002088.4-2310.
International Search Report and Written Opinion dated Apr. 21, 2010 issued in related International Patent Application No. PCT/US2010/025095.
International Search Report and Written Opinion dated May 3, 2010 issued in related International Patent Application No. PCT/US2010/025464.
European Office Action dated Apr. 13, 2010 issued in related European Patent Application No. 02805182.9-2310.
European Office Action dated Mar. 25, 2010 issued in related European Patent Application No. 01997077.1-2310.
Extended Search Report dated Jul. 3, 2012 issued in European Patent Application No. 12002103.5, 5 pages.
Decision to Grant dated Jul. 26, 2012 issued in European Patent Application No. 10012693.7, 1 page.
Final Office Action dated Aug. 13, 2012 issued in U.S. Appl. No. 12/711,039, 12 pages.
Office Action dated Aug. 14, 2012 issued in U.S. Appl. No. 12/001,473, 17 pages.
Office Action dated Aug. 20, 2012 issued in U.S. Appl. No. 13/037,998, 11 pages.
Office Action dated Aug. 21, 2012 issued in U.S. Appl. No. 13/043,430, 11 pages.
U.S. Office Action dated Aug. 28, 2012 issued in U.S. Appl. No. 12/762,948, 12 pages.
U.S. Notice of Allowance dated Sep. 4, 2012 issued in U.S. Appl. No. 11/169,326, 6 pages.
Notice of Allowability dated Oct. 9, 2012, issued in U.S. Appl. No. 12/713,135, 5 pages.
Notice of Allowability dated October11, 2012, issued in U.S. Appl. No. 11/169,326 2 pages.
U.S. Office Action dated Oct. 23, 2012, issued in U.S. Appl. No. 13/042,382, 17 pages.
U.S. Office Action dated Oct. 24, 2012, issued in U.S. Appl. No. 12/942,923, 9 pages.
U.S. Office Action dated Oct. 31 2012, issued in U.S. Appl. No. 13/075,006, 9 pages.
Notice of Allowance dated Nov. 13, 2012 issued in U.S. Appl. No. 12/725,181, 5 pages.
Preliminary Report on Patentability dated Sep. 20, 2012 issued in PCT Patent Application No. PCT/US2011/027451, 3 pages.
International Preliminary Report on Patentability dated Sep. 1, 2011 issued in PCT International Patent Application No. PCT/US2010/025095, 8 pages.
International Preliminary Report on Patentability dated Oct. 27, 2011 issued in PCT International Patent Application No. PCT/US2010/031602, 8 pages.
International Preliminary Report on Patentability dated Oct. 27, 2011 issued in PCT International Patent Application No. PCT/US2010/031594, 7 pages.
U.S. Office Action dated Nov. 1, 2011 issued in U.S. Appl. No. 12/713,135, 10 pages.
U.S. Notice of Allowance dated Nov. 23, 2011 issued in U.S. Appl. No. 11/623,513, 19 pages.
U.S. Office Action dated Nov. 28, 2011 issued in U.S. Appl. No. 12/711,039, 6 pages.
Notice of Allowance dated Dec. 12, 2011 issued in U.S. Appl. No. 12/582,345, 19 pages.
U.S. Office Action dated Dec. 22, 2011 issued in U.S. Appl. No. 11/623,513, 8 pages.
U.S. Office Action dated Dec. 27, 2011 issued in U.S. Appl. No. 12/620,309, 10 pages.
U.S. Office Action dated Jan. 4, 2012 issued in U.S. Appl. No. 12/001,473, 19 pages.
U.S. Office Action dated Jan. 10, 2012 issued in U.S. Appl. No. 12/031,534, 9 pages.
U.S. Office Action dated Jan. 18, 2012 issued in U.S. Appl. No. 12/778,055, 9 pages.
European Office Action dated Jan. 23, 2012 issued in European Patent Application No. 01 997 077.1, 3 pages.
Examination Report dated Dec. 30, 2011 issued in European Patent Application No. 09 002 088.4, 6 pages.
Intent to Grant dated Feb. 17, 2012 issued in European Patent Application No. 02 805 182.9, 5 pages.
Notice of Allowance dated Feb. 24, 2012 issued in U.S. Appl. No. 12/027,121, 9 pages.
Intent to Grant dated Feb. 29, 2012 issued in European Patent Application No. 10 012 693.7, 5 pages.
Supplemental Notice of Allowance dated Mar. 2, 2012 issued in U.S. Appl. No. 12/027,121, 2 pages.
Office Action dated Mar. 2, 2012 issued in U.S. Appl. No. 12/713,135, 7 pages.
U.S. Office Action dated Mar. 29, 2012 issued in U.S. Appl. No. 10/789,545, 7 pages.
U.S. Office Action dated Apr. 18, 2012 issued in U.S. Appl. No. 12/725,181, 9 pages.
U.S. Notice of Allowance dated May 31, 2012 issued in U.S. Appl. No. 11/623,513, 5 pages.
USPTO Office action dated Dec. 8, 2005 issued in corresponding U.S. Appl. No. 10/373,463.
USPTO Office Action dated Aug. 31, 2005 issued in corresponding U.S. Appl. No. 10/308,718.
USPTO Office action dated Aug. 16, 2005 issued in corresponding U.S. Appl. No. 10/373,463.
USPTO Office action dated Jan. 27, 2005 issued in corresponding U.S. Appl. No. 10/373,463.
USPTO Office action dated Aug. 13, 2004 issued in corresponding U.S. Appl. No. 10/373,463.
USPTO Notice of Allowance issued Sep. 26, 2003 in U.S. Appl. No. 10/162,533.
USPTO Notice of Allowance issued May 12, 2003 in U.S. Appl. No. 10/024,077.
USPTO Office Action dated Apr. 1, 2003 issued in U.S. Appl. No. 10/162,533.

(56) References Cited

OTHER PUBLICATIONS

USPTO Office action dated Mar. 28, 2003 issued in corresponding U.S. Appl. No. 10/024,077.
USPTO Notice of Allowance issued Sep. 30, 2002 in U.S. Appl. No. 09/846,657.
USPTO Office Action dated Apr. 2, 2002 issued in corresponding U.S. Appl. No. 09/846,657.
USPTO Office Action dated Feb. 27, 2002 issued in corresponding U.S. Appl. No. 09/846,657.
USPTO Office Action dated Jan. 3, 2002 issued in corresponding U.S. Appl. No. 09/846,657.
AU Examiners report dated Jan. 18, 2006 issued in corresponding Australian patnet application No. 2005202099.
AU Examiners report dated Jan. 12, 2007 issued in corresponding Australian patnet application No. 2006202337.
AU Examiners report dated Feb. 21, 2007 issued in corresponding Australian patnet application No. 2005202099.
AU Examiners report dated May 23, 2007 issued in corresponding Australian patnet application No. 2005202099.
AU Notice of Acceptance dated Aug. 6, 2007 in Patent Application No. 20022357284.
EPO supplementary partial search report dated May 10, 2004 issued in corresponding European application 01932833.5-231-/US0114061.
EPO supplementary search report dated Aug. 30, 2004 issued in corresponding European application 01932833.5.
EPO Office Action dated Aug. 23, 2004, received in related EPO application No. 03 026 286.9 (4 pgs).
EPO Office Action dated Mar. 15, 2005, received in related EPO application No. 03 026 286.9, (3 pgs).
EPO Search Report received in related EPO Application No. 03 02 6286.9 dated Feb. 26, 2004 (5pgs).
EPO Search Report received in related EPO Application No. 03 02 6286.9 dated Apr. 27, 2004 (6pgs).
Examination Report dated Feb. 22, 2005 received in corresponding European Application No. 01932833.5 (3pages).
EPO Office Action dated Sep. 22, 2005 issued in corresponding European application 01932833.5-2310.
EPO Office Action dated Sep. 11, 2006 issued in corresponding European application 01932833.5-2310.
International Preliminary Examination Report dated Nov. 5, 2002 issued in corresponding PCT patent application No. PCT/US01/14061.
US Office Action issued in related U.S. Appl. No. 10/994,453 dated Feb. 25, 2008.
International Preliminary Examination Report dated Nov. 12, 2002 issued in corresponding PCT patent application No. PCT/US01/48821.
International Preliminary Examination Report dated Sep. 12, 2003 issued in corresponding PCT patent application No. PCT/US02/40310.
International Preliminary Examination Report dated Oct. 27, 2003 issued in corresponding PCT patent application No. PCT/US01/48821.
International Preliminary Examination Report dated Aug. 19, 2004 issued in corresponding PCT patent application No. PCT/US02/40310.
Notice of Allowance issued in corresponding U.S. Appl. No. 10/618,887 dated Sep. 13, 2007.
International Preliminary Report on Patentability and Written Opinion dated May 22, 2006 in corresponding PCT patent application No. PCT/US04/039181.
English language translation of Japanese Office Action dated Aug. 9, 2007 issued in corresponding Japanese application No. 2003-552148.
Canadian Office Action dated Jan. 2, 2008 issued in corresponding Canadian Application No. 2407440.
International Preliminary Report on Patentability and Written Opinion dated Mar. 1, 2007 in corresponding PCT patent application No. PCT/US05/030120.
International Preliminary Report on Patentability and Written Opinion dated Jun. 28, 2007 in corresponding PCT patent application No. PCT/US2005/005980.
International Preliminary Report on Patentability and Written Opinion dated Jul. 19, 2007 in corresponding PCT patent application No. PCT/US2006/000380.
International Search Report dated Dec. 27, 2001 issued in corresponding PCT patent application No. PCT/US01/14061.
Office Action issued in corresponding U.S. Appl. No. 10/741,044 dated Oct. 26, 2005.
International Search Report dated May 23, 2003 issued in corresponding PCT patent application No. PCT/US02/40310.
International Search Report and Written Opinion dated Dec. 30, 2004 issued in corresponding PCT patent application No. PCT/US04/05539.
International Search Report and Written Opinion dated Jan. 30, 2006 issued in corresponding PCT patent application No. PCT/US04/39181.
International Search Report and Written Opinion dated Aug. 30, 2006 issued in corresponding PCT patent application No. PCT/US06/06323.
International Search Report and Written Opinion dated Sep. 29, 2006 issued in corresponding PCT patent application No. PCT/US05/30120.
International Search Report and Written Opinion dated Nov. 27, 2006 issued in corresponding PCT patent application No. PCT/US06/00380.
International Search Report and Written Opinion dated Nov. 29, 2006 issued in corresponding PCT patent application No. PCT/US05/023200.
International Search Report and Written Opinion dated May 22, 2007 issued in corresponding PCT patent application No. PCT/US05/05980.
Habermeyer, Peter, ATOS News, Oct. 2005, "The Artificial Limb "Eclipse"—A new draft without shank in the implantation of artificial shoulder limbs", cover page w/pp. 40-41, with English translation dated Jan. 13, 2006 (2 pgs).
Gray, Henry, Anatomy of the Human Body, 1918, 6d. The Foot 1. The Tarsus, II. Osteology, cover page and 10 pgs, www.Bartleby.com/107/63.html#i268 Oct. 25, 2004.
Chainsaw, Wikipedia, the free encyclopedia, http://en.wikipedia.org/w/index.php?title=Chainsaw&printable=yes, Jun. 26, 2007 (3 pages).
APTA | Knee,/http://www.apta.org/AM/PrinerTemplate.cfm?Section=Home&TEMPLATE=/CM/HTMLDisplay.dfg& . . . Jun. 25, 2007 (1page).
American Machinist, Full-radius milling cutters, http://www.americanmachinist.com/Classes/Article/ArticleDraw_P.aspx, Jun. 26, 2007 (1 page).
Chuck (engineering),Wikipedia, the free encyclopedia, http://en.wikipedia.org/w/index.php?title=Chuck_%28engineering%29&printable=yes, Jun. 25, 2007, (4 pages).
Dovetail Rails, http://www.siskiyou.com/MDRSeries.htm, Jun. 25, 2007 (2 pages).
Knee Resurfacing, Permedica, GKS, Global Knee System. Cod. 104570 vers 1.0 del Mar. 15, 2006 (8pages).
Makita Industrial Power Tools, Product Details Print Out, Chain Mortiser, http://www.makita.com/menu.php?pg=product_det_prn& tag=7104L, Jun. 26, 2007 (3pgs).
Milling machine, Wikipedia, the free encyclopedia, http://en.wikipedia.org/w/index.php?title=Milling_machine&printable=yes, Jun. 26, 2007 (4 pages).
Mortise and tenon, Wikipedia, the free encyclopedia, http://en.wikipedia.org/w/index.php?title=Mortise_and_tenon&printable=yes, Jun. 25, 2007 (3 pages).
Oka et al, "Development of artificial articular cartilage", Proc Instn Mech Engrs vol. 214 Part H, 2000 pp. 59-68 (10 pages).
M. Siguier, MD et al, "Preliminary Results of Partial Surface Replacement of the Femoral Head in Osteonecrosis", The Jorunal of Arthroplasty, vol. 14, No. 1, 1999, pp. 45-51.
T. Siguier, MD et al, Partial Resurfacing Arthroplasty of the Femoral Head in Avascular Necrosis', Clinical Orthopaedics and Related Research, No. 386, 2001, pp. 85-92.

(56) References Cited

OTHER PUBLICATIONS

Suganuma, et al—"Arthroscopically Assisted Treatment of Tibial Plateau Fractures", Arthroscopy: The Journal of Arthroscopic and Related Surgery, vol. 20, No. 10, Dec. 2004, pp. 1084-1089 (6 pages).
The Mini Uni: A New Solution for Arthritic Knee Pain and Disability, AORI, 4 pges, www.aori.org/uniknee.htm Apr. 20, 2004.
The Stone Clinic, Orthopaedic Surgery Sports Medicine and Rehabilitation, Unicompartmental Replacement (partial knee joint replacement), Aug. 21, 2000, 3 pages, www.stoneclinic.com/unicopartrepl.htm, Apr. 20, 2004.
Ushio et al, "Partial hemiarthroplasty for the treatment of osteonecrosis of the femoral head", An Experimantal Study in the Dog, The Journal of Bone and Joint Surgery, vol. 85-B, No. 6, Aug. 2003, pp. 922-930 (9 pages).
Russell E. Windsor, MD, In-Depth Topic Reviews, Unicompartmental Knee Replacement, Nov. 7, 2002, 9 pages.
Yaw angle, Wikipedia, the free encyclopedia, http://en.wikipedia.org/w/index.php?title=Yaw_angle&printable=yes, Jun. 25, 2007 (1 page).
Bale, MD, Reto J., et al, "Osteochondral Lesions of the Talus: Computer=assisted Retrograde Drilling Feasibility and Accuracy in Initial Experriencesl", (Radiology. 2001;218:278-282) © RSNA, 2001.
BioMet/Copeland, "Aequalis® Resurfacing Head" Tornier, Scientific Vision, Surgical Leadership, SS-401 Jan. 2007.
Kumai, M.D., Tsukasa, et al Arthroscopic Drilling for the Treatment of Osteochondral Lesions of the Talus*, The Journal of Bone & Joint Surgery, American vol. 81:1229-35(1999).
Matsusue, M.D., Yoshitaka, et al, "Arthroscopic Osteochondral Autograft Transplantation for Chondral Lesion of the Tibial Plateau of the Knee", Arthroscopy: The Journal of Arthroscopic and Related Surgery, vol. 17, No. 6 Jul.-Aug. 2001:pp. 653-659.
Pill M.S., P.T., Stephan G. et al, "Osteochondritis Dissecans of the Knee: Experiences at the Children's Hospital of Philadelphia and a Review of Literature", the University of Pennsylvania Orthopaedic Journal 14: 25-33, 2001.
Schneider, T., et al, "Arthroscopy of the ankle joint. A list of indications and realistic expectations", Foot and Ankle Surgery 1996 2:189-193, © 1996 Arnette Blackwell SA.
Taranow WS, et al, "Retrograde drilling of osteochondral lesions of the medial talar dome", PubMed, www.pubmed.gov, A service of the National Library of Medicing and the Natinal Institutes of Health, Foot Ankle Int.Aug. 1999; 20(8):474-80.
Ueblacker, M.D., Peter, et al, "Retrograde Cartilage Transplantation of the Proximal and Distal Tibia", Arthroscopy: The Journal of Arthroscipic and Related Surgery, vol. 20, No. 1 Jan. 2004: pp. 73-78.
USPTO Office Action dated Dec. 21, 2007 issued in corresponding U.S. Appl. No. 11/169,326.
USPTO Office Action dated Dec. 26, 2007 issued in U.S. Appl. No. 11/379,151.
USPTO Office Action dated Oct. 9, 2007 issued in U.S. Appl. No. 10/373,463.
USPTO Office Action dated Aug. 29, 2007 issued in U.S. Appl. No. 10/760,965.
USPTO Office Action dated May 31, 2007 issued in corresponding U.S. Appl. No. 11/326,133.
USPTO Office Action dated Apr. 26, 2007 issued in U.S. Appl. No. 10/373,463.
USPTO Office Action dated Apr. 4, 2007 issued in corresponding U.S. Appl. No. 10/789,545.
USPTO Office Action dated Mar. 15, 2007 issued in U.S. Appl. No. 10/760,965.
USPTO Office Action dated Feb. 20, 2007 issued in corresponding U.S. Appl. No. 11/326,133.
USPTO Office Action dated Nov. 6, 2006 issued in U.S. Appl. No. 10/760,965.
USPTO Office Action dated Oct. 17, 2006 issued in U.S. Appl. No. 10/373,463.
USPTO Office Action dated Oct. 31, 2006 issued in U.S. Appl. No. 10/760,965.
USPTO Office Action dated Jul. 25, 2006 issued in U.S. Appl. No. 10/760,965.
USPTO Office action dated May 10, 2006 issued in corresponding U.S. Appl. No. 10/373,463.
USPTO Office Action dated Apr. 21, 2006 issued in corresponding U.S. Appl. No. 10/308,718.
USPTO Office Action dated Nov. 9, 2005 issued in corresponding U.S. Appl. No. 10/308,718.
Extended European Search report mailed Dec. 10, 2012 issued in European Patent Application No. 07844549.1, 6 pages.
Supplementary European Search Report dated Jan. 3, 2013 issued in European Patent Application No. 05763817.3, 3 pages.
Great Britain Examination Report dated Feb. 6, 2013 issued in Great Britain Patent Application No. 1114417.7, 2 pages.
Supplementary European Search Report dated Feb. 18, 2013 issued in European Patent Application No. 08729178.7, 10 pages.
U.S. Office Action dated Feb. 25, 2013 issued in U.S. Appl. No. 12/762,920, 8 pages.
U.S. Office Action dated Jul. 11, 2013 issued in U.S. Appl. No. 12/711,039, 10 pages.
U.S. Notice of Allowance dated Jul. 29, 2013 issued in U.S. Appl. No. 12/725,181, 7 pages.
U.S. Final Office Action dated Jul. 30, 2013 issued in U.S. Appl. No. 13/075,006, 10 pages.
U.S. Corrected Notice of Allowance dated Jul. 30, 2013 issued in U.S. Appl. No. 11/623,513, 2 pages.
Corrected Notice of Allowability dated Sep. 10, 2013 issued in U.S. Appl. No. 13/043,430, 7 pages.
Canadian Office Action dated Dec. 13, 2012 issued in Canadian Patent Application No. 2,407,440, 6 pages.
International Search Repoort and Written Opinion dated Mar. 8, 2013 issued in PCT Patent Application No. PCT/US12/71199, 13 pages.
U.S. Office Action dated Apr. 22, 2013 issued in U.S. Appl. No. 12/001,473, 16 pages.
U.S. Office Action dated Apr. 23, 2013 issued in U.S. Appl. No. 13/037,998, 8 pages.
European Intent to Grant dated Apr. 29, 2013 issued in European Patent Application No. 07 862 736.1, 7 pages.
U.S. Notice of Allowance dated May 9, 2013 issued in U.S. Appl. No. 12/725,181, 6 pages.
U.S. Office Action dated May 15, 2013 issued in U.S. Appl. No. 12/762,948, 10 pages.
European Office Action dated Apr. 16, 2013 issued in European Patent Application No. 12 002 103.5, 5 pages.
European Office Action dated May 15, 2013 issued in European Patent Application No. 05 763 817.3, 4 pages.
Decision to Grant dated Sep. 19, 2013 issued in European Patent Application No. 07862736.1, 1 page.
U.S. Applicant Initiated Interview Summary dated May 15, 2013 issued in U.S. Appl. No. 12/762,920, 3 pages.
U.S. Final Office Action dated Jun. 5, 2013 issued in U.S. Appl. No. 12/942,923, 26 pages.
U.S. Final Office Action dated Jun. 24, 2013 issued in U.S. Appl. No. 13/042,382, 28 pages.
U.S. Notice of Allowance dated Jun. 14, 2013 issued in U.S. Appl. No. 13/043,430, 10 pages.
U.S. Office Action dated Feb. 5, 2014, issued in U.S. Appl. No. 13/438,095, 9 pages.
U.S. Office Action dated Feb. 7, 2014, issued in U.S. Appl. No. 13/075,006, 9 pages.
Australian Examination Report dated Feb. 7, 2014, issued in Australian Patent Application No. 2010236182, 3 pages.
Australian Examination Report dated Feb. 14, 2014, issued in Australian Patent Application No. 2011222404, 3 pages.
European Extended Search Report dated Feb. 24, 2014, issue in European Patent Application No. 09716273.9, 7 pages.
Australian Examination Report dated Feb. 28, 2014, issued in Australian Patent Application No. 2010217907, 3 pages.
U.S. Final Office Action dated Mar. 20, 2014, issued in U.S. Appl. No. 12/711,039, 17 pages.
European Examination Report dated Mar. 20, 2014, issued in European Patent Application No. 12 002 103.5, 3 pages.

(56) References Cited

OTHER PUBLICATIONS

U.S. Office Action dated Mar. 21, 2014, issued in U.S. Appl. No. 12/942,923, 6 pages.
Australian Examination Report dated Apr. 3, 2014, issued in Australian Patent Application No. 2010217907, 3 pages.
U.S. Office Action dated Oct. 8, 2013 issued in U.S. Appl. No. 13/438,095, 8 pages.
International Search Report and Written Opinion dated Oct. 22, 2013 issued in PCT International Patent Application No. PCT/US2013/048569, 15 pages.
Notice of Allowance dated Oct. 30, 2013 issued in U.S. Appl. No. 13/037,998, 28 pages.
U.S. Final Office Action dated Nov. 29, 2013 issued in U.S. Appl. No. 12/762,920, 9 pages.
U.S. Office Action dated Dec. 12, 2013 issued in U.S. Appl. No. 12/979,992, 12 pages.
U.S. Office Action dated Dec. 17, 2013 issued in U.S. Appl. No. 12/001,473, 21 pages.
U.S. Office Action dated Apr. 29, 2014, issued in U.S. Appl. No. 13/037,929, 11 pages.
U.S. Office Action dated May 19, 2014, issued in U.S. Appl. No. 13/436,188, 10 pages.
U.S. Office Action dated May 28 2014, issued in U.S. Appl. No. 13/752,858, 8 pages.
U.S. Office Action dated Jun. 4, 2014, issued in U.S. Appl. No. 12/762,920, 10 pages.
U.S. Office Action dated Jul. 7, 2014, issued in U.S. Appl. No. 12/979,992, 6 pages.
U.S. Office Action dated Jul. 7, 2014, issued in U.S. Appl. No. 12/001,473, 15 pages.
Intent to Grant dated Jun. 27, 2014, issued in European Patent Application No. 12 002 103.5, 6 pages.
U.S. Office Action dated Aug. 13, 2014, issued in U.S. Appl. No. 12/762,948, 12 pages.
U.S. Notice of Allowance dated Aug. 21, 2014, issued in U.S. Appl. No. 13/075,006, 5 pages.

* cited by examiner

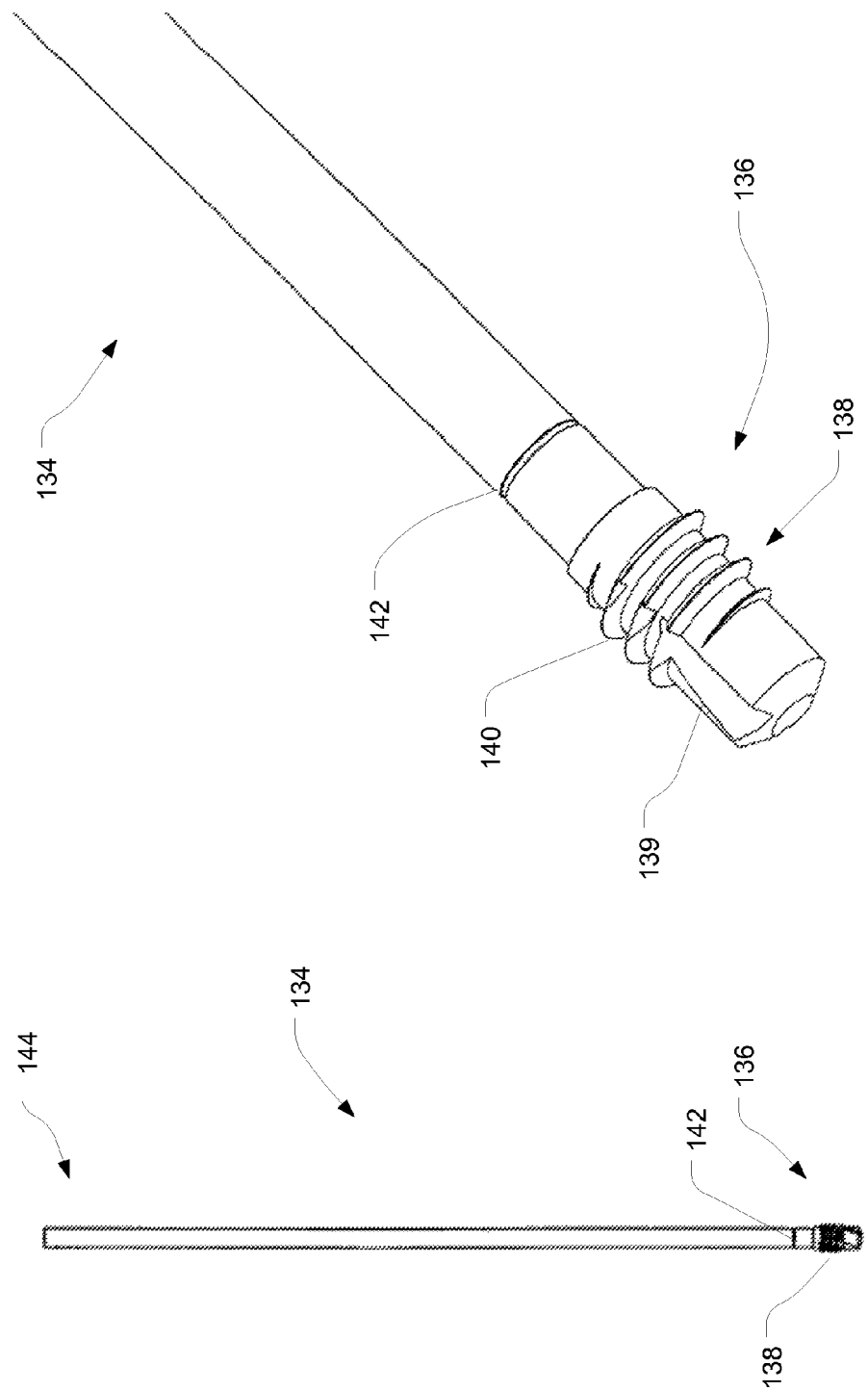

SYSTEM AND METHOD FOR JOINT RESURFACE REPAIR

CROSS REFERENCE TO RELATED APPLICATIONS

This application is a continuation of U.S. patent application Ser. No. 12/027,121 (now U.S. Pat. No. 8,177,841), filed Feb. 6, 2008, which claims the benefit of U.S. Provisional Patent Application Ser. No. 60/888,382, filed Feb. 6, 2007. U.S. patent application Ser. No. 12/027,121 (now U.S. Pat. No. 8,177,841), filed Feb. 6, 2008, is also a continuation-in-part of U.S. patent application Ser. No. 11/359,891 (now U.S. Pat. No. 7,713,305), filed Feb. 22, 2006, which itself is a continuation-in-part of U.S. patent application Ser. No. 10/373,463 (now U.S. Pat. No. 7,678,151), filed Feb. 24, 2003, which is a continuation-in-part application of U.S. patent application Ser. No. 10/162,533 (now U.S. Pat. No. 6,679,917), filed Jun. 4, 2002, which is itself a continuation-in-part application of U.S. patent application Ser. No. 10/024,077 (now U.S. Pat. No. 6,610,067), filed Dec. 17, 2001, which is itself a continuation-in-part application of U.S. patent application Ser. No. 09/846,657 (now U.S. Pat. No. 6,520,964), filed May 1, 2001, which claims the benefit of U.S. Provisional Patent Application Ser. No. 60/201,049, filed May 1, 2000, all of which are incorporated herein by reference. The entire disclosures of all of the above-identified applications/patents are incorporated herein by reference.

FIELD

This disclosure relates to devices and methods for the repair of defects that occur in articular cartilage on the surface of bones, particularly the knee.

BACKGROUND

Articular cartilage, found at the ends of articulating bone in the body, is typically composed of hyaline cartilage, which has many unique properties that allow it to function effectively as a smooth and lubricious load-bearing surface. When injured, however, hyaline cartilage cells are not typically replaced by new hyaline cartilage cells. Healing is dependent upon the occurrence of bleeding from the underlying bone and formation of scar or reparative cartilage called fibrocartilage. While similar, fibrocartilage does not possess the same unique aspects of native hyaline cartilage and tends to be far less durable.

In some cases, it may be necessary or desirable to repair the damaged articular cartilage using an implant. While implants may be successfully used, the implant should have a shape substantially corresponding to the articular cartilage proximate the area where the implant is to be placed in order to maximize the patient's comfort, minimize damage to surrounding areas, and maximize the functional life of the implant.

BRIEF DESCRIPTION OF DRAWINGS

The advantages and features of the present disclosure will become better understood with reference to the following detailed description and claims taken in conjunction with the accompanying drawings, wherein like elements are identified with like symbols, and in which:

FIG. 6 illustrates a plan side view of one embodiment of a guide pin.

FIG. 7 is a close-up of the distal end of the guide pin shown in FIG. 6.

DETAILED DESCRIPTION

Figure 1:
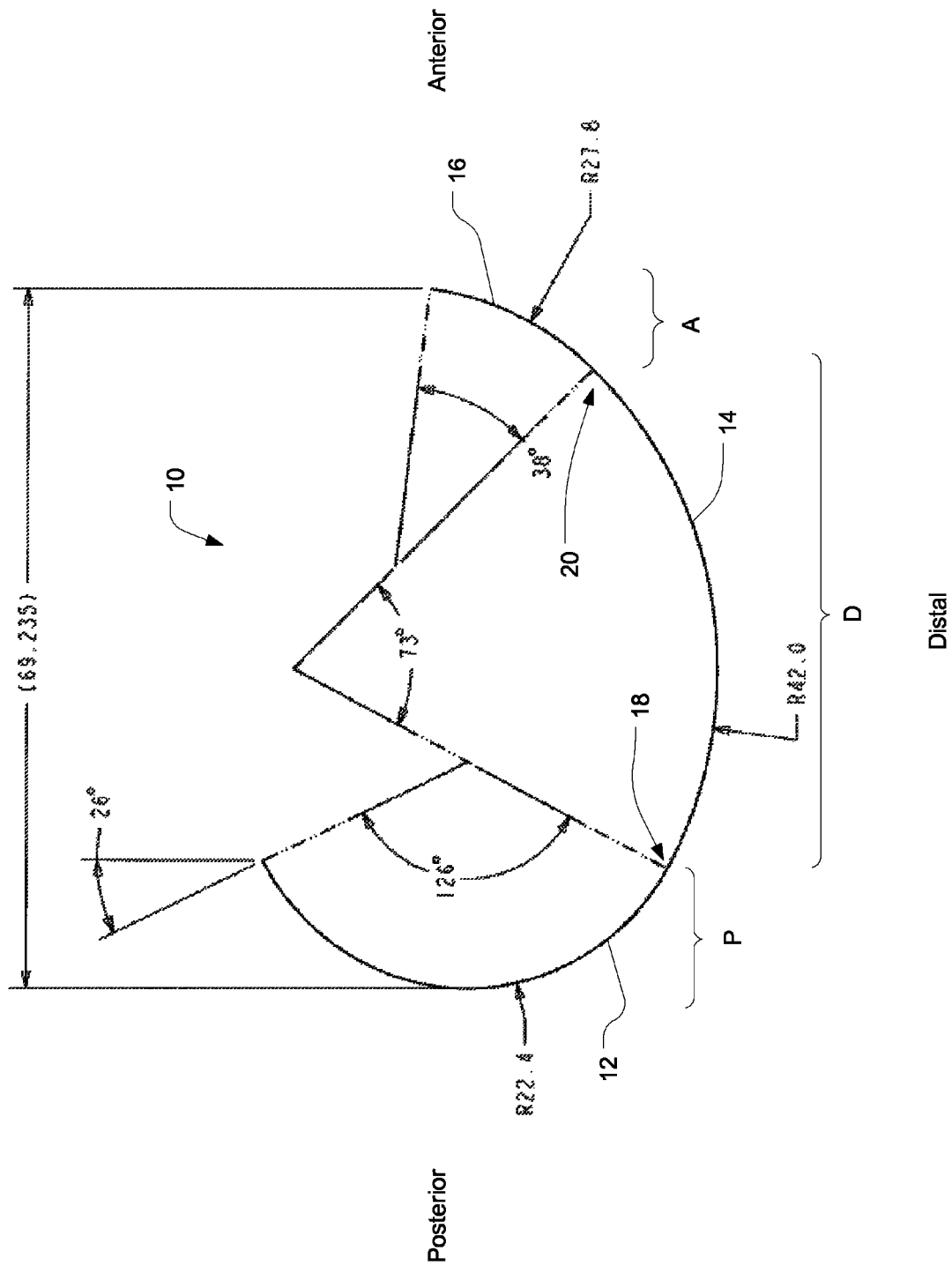
FIG. 1 illustrates the anterior-posterior (AP) curvature 10 of a typical femoral condyle.

FIG. 1 depicts the anterior-posterior (AP) curvature 10 of a typical femoral condyle. The curve 10 depicted in this figure may be representative of an average of AP curves from a plurality of individuals. Such curvature values may be readily found in published medical literature, for example, as may be reported in "Clinical Biomechanics 18," 2003, N. Nuno and A. M. Ahmed, which is fully incorporated herein by reference. As can be seen in this Figure, the AP curvature 10 of the articular surface may generally include a plurality of tangential curves having different radii of curvature.

For example, as shown in this figure, curve 10 may include a first or posterior curve 12 extending generally along the posterior region P of the femoral condyle. Curve 10 may also include a second or distal curve 14 extending generally along the distal region D of the femoral condyle), and a third or anterior curve 16 extending generally along the anterior region A of the femoral condyle. The first and second curves 12, 14 may be approximately tangential about tangent point 18 and the second and third curves 14, 16 may be approximately tangential about tangent point 20. The tangent points 18, are only approximations, and the exact location of the tangent points 18, 20 may vary.

For exemplary purposes, while the AP curvature 10 may vary amongst individuals, the posterior curve 12 may have span approximately 126 degrees, the distal curve 14 may span approximately 73 degrees, and the anterior curve 16 may span approximately 38 degrees. Again, it should be noted that the extent of these curvatures may vary widely amongst individuals, and these specific ranges are provided for exemplary purposes only.

One aspect of the present disclosure is directed towards an implant that approximates at least a portion of the AP curvature 10 depicted in FIG. 1. For example, for a defect that spans at least part of the distal and posterior regions of the AP curve 10, an implant provided by the present disclosure may be configured to accommodate the posterior curvature 12 and the distal curvature 14 of the femoral condyle. Advantageously, and as will be described more fully below, the implant of the present disclosure may have an AP curvature that is defined using a minimal number of data points along the AP extent of the femoral condyle. This feature may enable, for example, minimally invasive measurement procedures and implant site preparation, in accordance with previous disclosures incorporated by reference herein.

Figure 2:
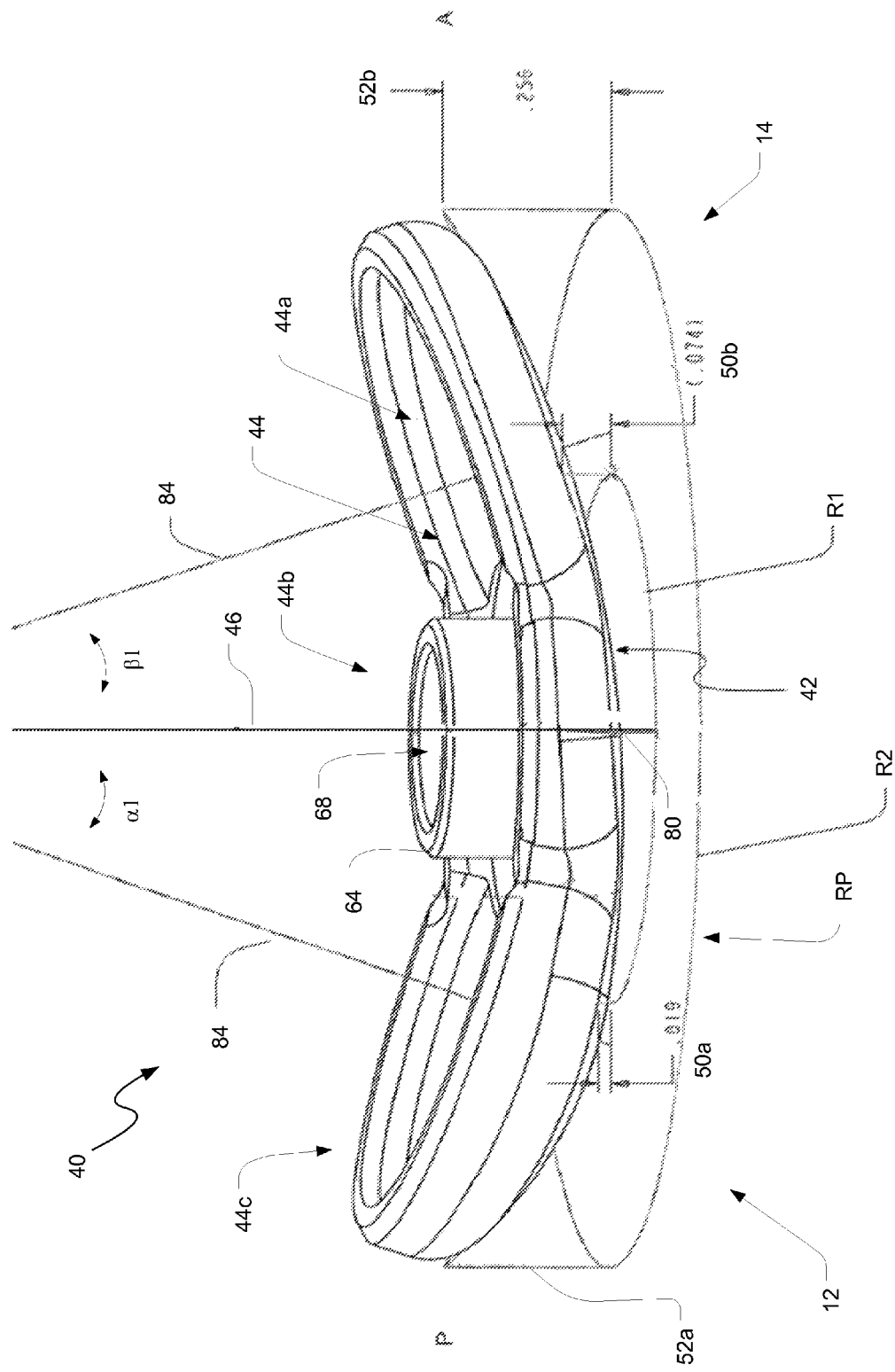
FIG. 2 illustrates an isometric side view of one embodiment of an implant.
Figure 3:
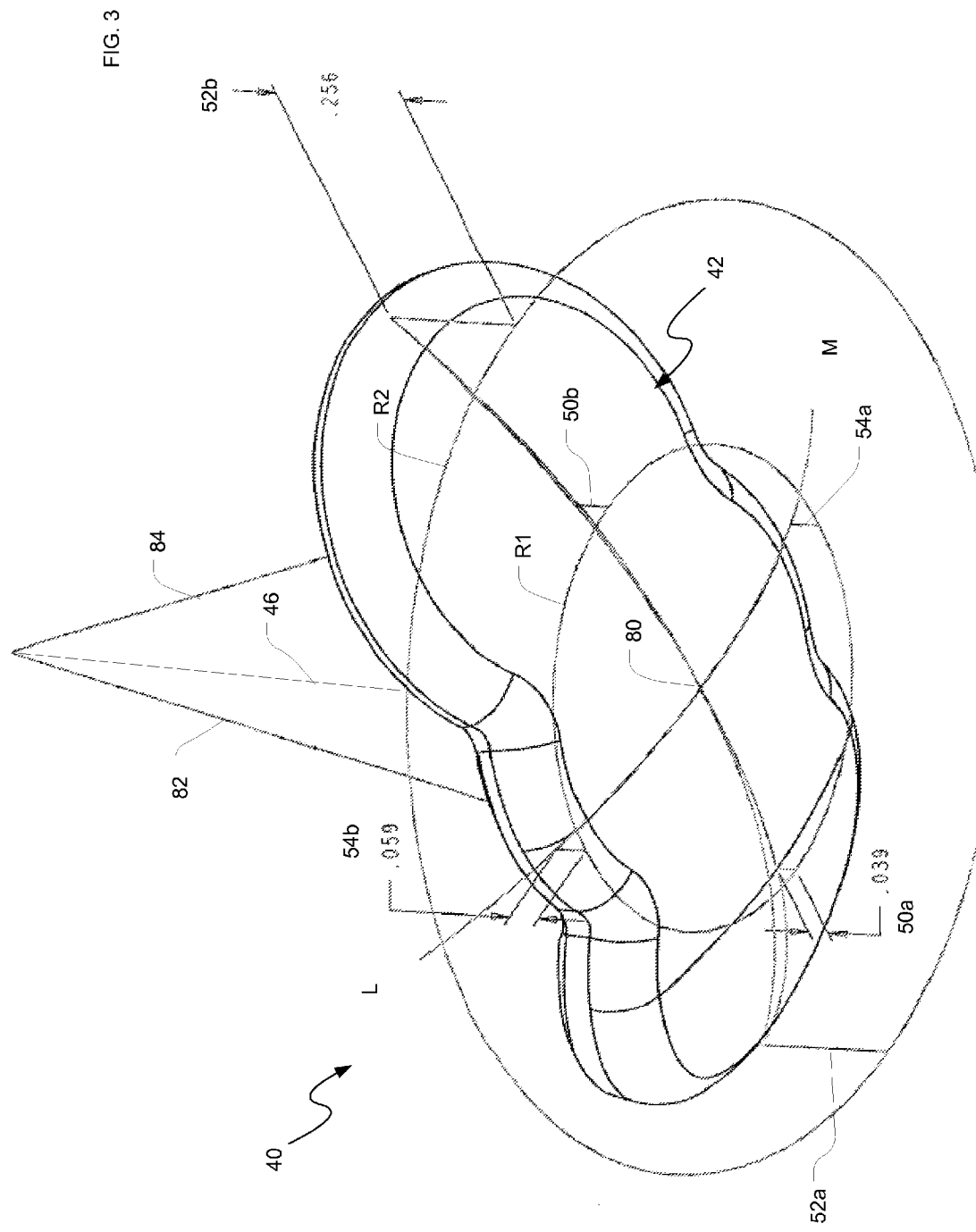
FIG. 3 illustrates an isometric bottom view of the implant shown in FIG. 2.

FIGS. 2 and 3 depict an implant according to one aspect of the present disclosure. FIG. 2 depicts an isometric side view of an implant 40. The implant 40 may include a load bearing (distal) surface 42 and a bone contacting surface 44. Surface 44 may include, for example, three or more segments 44a, 44b, 44c. In this embodiment, the implant 40 has an extended length along the AP dimension. In other words, implant 40 is generally longer in the AP dimension than the medial lateral (ML) dimension. For purposes of this example, it is assumed that the implant 40 is to be placed along a region that covers at least part of both the posterior curvature 12 and the distal curvature 14 of the femoral condyle depicted in FIG. 1. However, it is equally contemplated herein that the implant 40 may be configured to define a curvature anywhere along the AP curve 10 depicted in FIG. 1.

As a general statement, the curvature of the load bearing or distal surface 42 of the implant 40 may be defined by the depth from a reference plane (RP) to the load bearing surface 42 of the implant 40 at two or more different locations along the AP extent of the implant 40. In the example of FIG. 2, reference plane RP is generally tangent to the load bearing surface 42 at a point 80 that passes through the reference axis 46. Reference plane RP may also be parallel to a tangential plane extending through the point 80 (e.g., the reference plane RP may be parallel to and offset a distance X from the tangent plane passing through point 80). Point 80 may be defined as a point of origin from which depth measurements may be defined. Reference axis 46 may pass through at generally the midpoint of the implant 40, i.e., through the middle of segment 44b.

According to one embodiment, at least one depth 50a and/or 50b from the reference plane RP to the surface 42 may be defined at a first distance R1 from the reference axis 46. At least one additional depth 52a and/or 52b from the reference plane RP to the surface 42 may be defined at a second distance R2 from the reference axis 46. As shown in this example, the first distance R1 is illustrated as a first circle centered about the reference axis 46 in the reference plane RP. Also as shown in this example, the second distance R2 is illustrated as a second circle centered about the reference axis 46 in the reference plane RP, where R1<R2. Reference axis 46 may pass through at generally the midpoint of the implant 40, i.e., through the middle of segment 44b Two or more depths, namely, at least one depth 50a and/or 50b taken at distance R1 and at least a second depth 52a and/or 52b taken at distance R2 from the reference axis 46. For example, the depth 50a may be defined as a distance between the reference plane RP and the surface 42 at a point between the reference axis 46 and the posterior (P) end of the implant 40, while depth 50b may be defined as a distance between the reference plane RP and the surface 42 at a point between the reference axis 46 and the anterior (A) end of the implant 40. Additionally, the depth 52a may be defined as a distance between the reference plane RP and the surface 42 at a point near the posterior (P) end of the implant 40, while depth 52b may be defined as a distance between the reference plane RP and the surface 42 near the anterior (A) end of the implant 40.

In one exemplary embodiment, depths 52a and 52b may be assumed approximately equal. In this case, only one depth 52a or 52b may be defined, and thus, the curvature of surface 42 of the implant 40 may be approximated using depths 52a or 52b and at least one of 50a and/or 50b. The foregoing assumes that the reference axis 46 is approximately normal to the articular surface. However, in alternative embodiments, if the reference axis is not assumed normal to the articular surface, then both depths 52a and 52b may be used to define the AP curvature of the surface 42 of the implant 40.

Each segment 44a and 44c, by virtue of the AP curvature defined by data points 50a, 50b, 52a, and/or 52b, may also have a reference axis 84 and 82, respectively. Reference axis 82 may be substantially normal to the articular surface and substantially normal to the outer surface 42 of segment 44c and passing through approximately the middle of segment 44c. Likewise, reference axis 84 may be substantially normal to the articular surface and substantially normal to the outer surface 42 of segment 44a and passing through approximately the middle of segment 44a. Since data points 52a and 52b may be approximately equal and implant 40 may be symmetrical about reference axis 46, the angle between reference axis 82 and 46, denoted as $\alpha_1$ in FIG. 2, and the angle between reference axis 84 and 46, denoted as $\beta_1$ in FIG. 2, may therefore be approximately equal.

Thus, by defining the AP curvature of surface 42 of the implant 40 in a manner described above, the curvature of surface 42 may include two (or more) tangential, but distinct, curves of the femoral condyle. It should be noted that in most cases, the values of depth 50a and 50b may be inversely related. Thus, in a typical scenario, as the value of 50a increases, the value of 50b may decrease, and vice-versa.

As mentioned above, the implant 40 may include three or more segments 44a, 44b, 44c, wherein each segment 44a, 44b, 44c has a reference axis 82, 46, 84, respectively. The first and the third segments 44a, 44c may partially overlap the second segment 44b about opposing ends of the second segment 44b. In other words, the second segment 44b may partially overlap with each of the adjacent segments 44a and 44c. As shown, one or more of the segments 44a, 44b, 44c may include generally circular cross-sectional shape which has been truncated along the AP extent of the implant 40. In addition, any of the segments 44a, 44b, 44c may be truncated along the ML extent of the implant 40 as well.

The distal or bone facing surface 42 of the implant 40 may include one or more mounting features or fixation elements 64 for securing the implant 40 to the femoral condyle. For example, the mounting feature 64 may be configured to engage with a screw or the like (not shown) as described in U.S. application Ser. No. 10/373,463 filed Feb. 24, 2003, U.S. Pat. No. 6,679,917 issued Jan. 20, 2004, U.S. Pat. No. 6,610,067 issued Aug. 26, 2003, U.S. Pat. No. 6,520,964 issued Feb. 18, 2003, and U.S. Provisional Application Ser. No. 60/201,049 filed May 1, 2000, all of which are fully incorporated herein by reference. As shown, the mounting feature 64 may include an opening 68 (such as, but not limited to, a tapered opening) configured to engage with a corresponding post (not shown) of a screw. The opening 68 may be formed in a protrusion or the like extending generally outwardly from the bone facing surface 44. Other configurations for securing the implant 40 to the femoral condyle are also possible and contemplated herein.

As shown, the mounting feature 64 may be disposed in the second segment 44b. However, one or more mounting features 64 may be provided in the first, second, and/or third segments 44a, 44b, 44c. Optionally, the mounting feature 64 (for example, the opening 68) may be axially aligned with at least one of the axes 46, 82, 84. As shown, opening 68 of the mounting feature 64 may be axially aligned with the reference axis 46.

FIG. 3 depicts an isometric bottom view of the implant 40. The AP curvature of the implant 40 may be defined as described above. The ML curvature of the implant 40 may be defined by at least two depths 54a and 54b taken at a distance from the reference axis 46. For example, depth 54a may be defined as a distance between the reference plane RP and the surface 42 at a point near the medial (M) end of the implant 40, while depth 54b may be defined as a distance between the reference plane RP and the surface 42 near the lateral (L) end of the implant 40. Based on these depths, the ML curvature of the surface 42 may be approximated as described in U.S. application Ser. No. 10/373,463 filed Feb. 24, 2003, U.S. Pat. No. 6,679,917 issued Jan. 20, 2004, U.S. Pat. No. 6,610,067 issued Aug. 26, 2003, U.S. Pat. No. 6,520,964 issued Feb. 18, 2003, and U.S. Provisional Application Ser. No. 60/201,049 filed May 1, 2000, all of which are fully incorporated herein by reference.

In one embodiment, the system of the present disclosure may include a kit that includes a plurality of implants 40 having various AP curvatures and optionally various ML curvatures as described above. The set of implants may be based on the most common values for the AP and ML curvatures based on the most likely femoral condyle implantation sites as well as most likely values for the various depths along the AP and ML curvatures described above. For example, in such a set of implants, one or more of the AP depth values 50a, 50b, 52a, and/or 52b may vary from one implant to the next implant, for example, in ½ mm increments. In this case, an implant may be selected that most closely matches the measurements obtained from the patient's articular surface as described briefly below. Alternatively, a custom-built implant may be fabricated using these depth values.

Obtaining the depth measurements along the AP curvature and ML curvature may be obtained using the measuring tool/outrigger as described in application Ser. No. 10/373,463 filed Feb. 24, 2003, U.S. Pat. No. 6,679,917 issued Jan. 20, 2004, U.S. Pat. No. 6,610,067 issued Aug. 26, 2003, U.S. Pat. No. 6,520,964 issued Feb. 18, 2003, and U.S. Provisional Application Ser. No. 60/201,049 filed May 1, 2000, all of which are fully incorporated herein by reference.

However, in the case of the AP depth measurements, rather than using a single measuring tool, two measuring tools may be used. For example, a first measuring tool/outrigger having a radius of R1 may be used to obtain depth values 50a and/or 50b and a second measuring tool/outrigger having a radius of R2 may be used to obtain the depth values 52a and/or 52b, wherein R2>R1. Of course, the methodology described in the aforementioned U.S. patents may be utilized using a single common reference axis (e.g., axis 46) to obtain all the measurements described herein.

The implant 40 according to the present disclosure, may be secured to the patient's articular surface as described in application Ser. No. 10/373,463 filed Feb. 24, 2003, U.S. Pat. No. 6,679,917 issued Jan. 20, 2004, U.S. Pat. No. 6,610,067 issued Aug. 26, 2003, U.S. Pat. No. 6,520,964 issued Feb. 18, 2003, and U.S. Provisional Application Ser. No. 60/201,049 filed May 1, 2000 hereby incorporated by reference.

Figure 4:
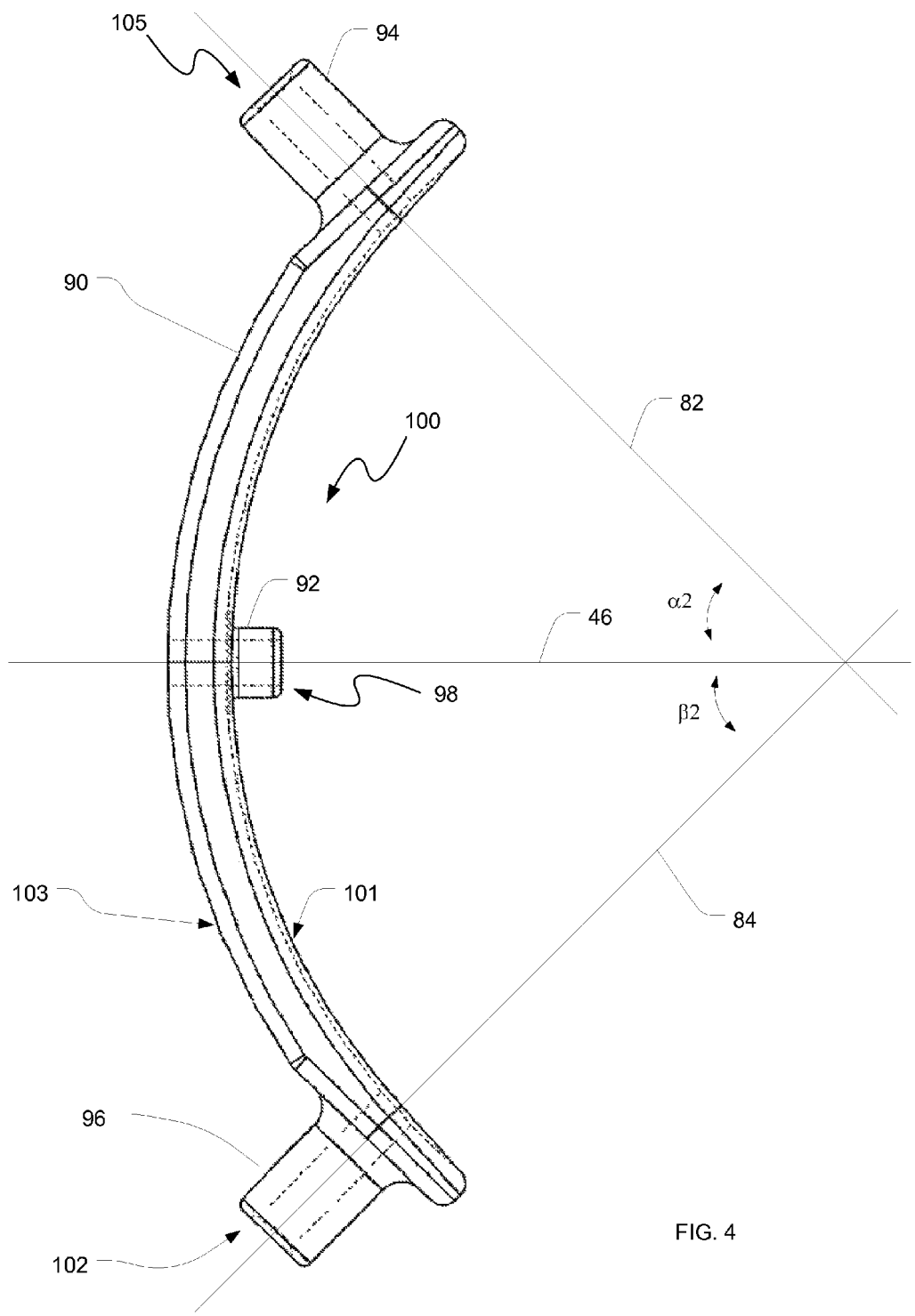
FIG. 4 illustrates a plan side view of one embodiment of a drill guide.

FIG. 4 depicts a drill guide 100 consistent with another aspect of the present disclosure. Drill guide 100 may be used to establish a plurality of axes used to create a plurality of excision sites, for example, excision sites in the articular surface corresponding to segments 44a, 44b and 44c of the implant 40. The use of a multi-axes drill guide is described in U.S. patent application Ser. No. 11/169,326 (US 2006/0020343) filed Jun. 28, 2005 hereby incorporated by reference in its entirety. As will be explained below, the drill guide 100 may be used to establish a plurality of axes 46, 82, 84 with respect to the articular surface. Axes 46, 82 and 84 may be related to one another which may be used to guide a cutting instrument when forming the excision sites in the articular surface for the implant 40.

The drill guide 100 may be selected based on the data points obtained from the articular surface (described above). As with the implant 40 described above, the system of the present disclosure may include a kit that includes a plurality of drill guides 100 that correspond (approximately) to the data points obtained so that the angles $\alpha_2$ and $\beta_2$ substantially correspond to the angles $\alpha_1$ and $\beta_2$ of the implant 40. To that end, the curvature of the drill guides 100 included in such a kit will vary from one to the next, in order to establish the proper working axes 82 and 84.

Consistent with one embodiment, the drill guide 100 may generally include a body portion 90 having a generally arcuate shape in which at least a portion of the interior surface 101 of the drill guide 100 may be configured to be disposed on at least a portion of an articular surface where the implant site is to be provided. The drill guide 100 may also include a first, a second, and a third drill bushing 92, 94, and 96. The first drill bushing 92 may be configured to be disposed on the interior surface 101 of the drill guide body 90 and may extend generally radially inwardly from the drill guide 100. According to one embodiment, the first drill bushing 92 may optionally have an outer diameter that substantially corresponds to a hole drilled into the articular surface which may be used to index the drill guide 100 on the articular surface as will be discussed below. The first drill bushing 92 may also include an opening or boss 98 extending through the drill guide 100 and the first drill bushing 92. A longitudinal axis of the opening 98 in the first drill bushing 94 may substantially correspond to the reference axis 46. The first drill bushing 92 may optionally include a separate component from the body portion 90 of the drill guide 100 and may be configured to be removably coupled to the body portion 90 of the drill guide 100.

The second and third drill bushings 94, 96 may be disposed on the outer surface 103 of the drill guide body 90 and may be a spaced distance from the first drill bushing 92. The spacing of the second and third drill bushings 94, 96 may be determined based on the size of the segments 44a, 44b and 44c relative to one another, which, in turn, correspond to the excision sites in the articular surface. The measurements define the AP curve, which determines the drill guide 100 to select the angular relationship of the three axes. According to one embodiment, the second and third drill bushings 94, 96 may optionally extend generally radially outwardly from the drill guide 100. The second and third drill bushings 94, 96 may also each include an opening or boss extending through the drill guide 100 and the second and third drill bushings 94, 96. Longitudinal axes of the openings 105 and 102 may substantially correspond to the working axis 82, 84, respectively, similar to working or reference axis 46. One or more of the second and third drill bushings 94, 96 may optionally include a separate component from the body portion 90 of the drill guide 100 and may be configured to be removably coupled to the body portion 90 of the drill guide 100.

As is taught in the aforementioned published patent application, the drill guide 100 may be coordinated or indexed with the location element installed in the articular surface so that the first drill bushing 92 may be oriented coaxial with the reference axis 46 defined by the location element. For example, a guide rod may be fitted extending from the location element, and the guide rod may be received through the opening 98 in the first drill bushing 92 of the drill guide 100. According to such an embodiment, the guide rod and the location element may be provided having mating features, such as mating precision tapers. The guide rod may, therefore, be aligned along the reference axis 46. Alternatively, the drill guide 100 and the location element may include cooperating features allowing the drill guide 100 and location element to be coordinated, e.g. aligned, positioned, etc., in a predetermined manner. The first drill bushing 92 may bear against, or otherwise interact with, the location element to position the drill guide 100 at a predetermined height relative to the articular surface, based on the height of the location element relative to the articular surface.

According to a related alternative embodiment, the drill guide 100 may be indexed or positioned on the articular surface without the use of a location element. Consistent with one such embodiment, the reference axis 46 may be established, for example as described above, and a hole may be drilled into the articular surface generally along the reference axis 46. The first drill bushing 92 may be sized and shaped to be at least partially received in the hole drilled into the articular surface about the reference axis 46. The respective sizes of the hole and the first drill bushing 92 may be coordinated to achieve a predetermined tolerance and control the amount of movement, or slop, of the drill guide 100 relative to the articular surface. In one embodiment, a snug fit may be achieved between the first drill bushing 92 and the hole, thereby restricting movement of the drill guide 100 relative to the articular surface.

With the drill guide 100 located on the articular surface and indexed with the reference axis 46, the working axes 82 and 84 may be established relative to the articular surface and the reference axis 46. The working axes 82, 84 may be established by drilling reference holes into the articular surface guided by the second and third drill bushings 94 and 96. A location element may be installed into each of the reference holes created in the articular surface using the second and third drill bushings 94, 96 of the drill guide 100 as described in application Ser. No. 10/373,463 filed Feb. 24, 2003, U.S. Pat. No. 6,679,917 issued Jan. 20, 2004, U.S. Pat. No. 6,610,067 issued Aug. 26, 2003, U.S. Pat. No. 6,520,964 issued Feb. 18, 2003, and U.S. Provisional Application Ser. No. 60/201,049 filed May 1, 2000.

Once the working axes 82 and 84 and the reference axis 46 have been established, portions of the articular surface (and optionally underlying subchondral bone) may be excised to provide excision sites corresponding to segments 44a, 44b and 44c of the implant 40. According to one embodiment, the articular surface may be excised using a drill, rotating cutter, or other instrument for excising a generally circular region of the articular surface and/or subchondral bone as described in application Ser. No. 10/373,463 filed Feb. 24, 2003, U.S. Pat. No. 6,679,917 issued Jan. 20, 2004, U.S. Pat. No. 6,610,067 issued Aug. 26, 2003, U.S. Pat. No. 6,520,964 issued Feb. 18, 2003, and U.S. Provisional Application Ser. No. 60/201,049 filed May 1, 2000. Depending upon the diameter of the cutting path defined by the cutting blade or blades of the cutting instrument, at least a portion of the cutting path defined by the sweep of the cutting instrument may extend outside of the width of the condyle at the excision site.

Figure 5:
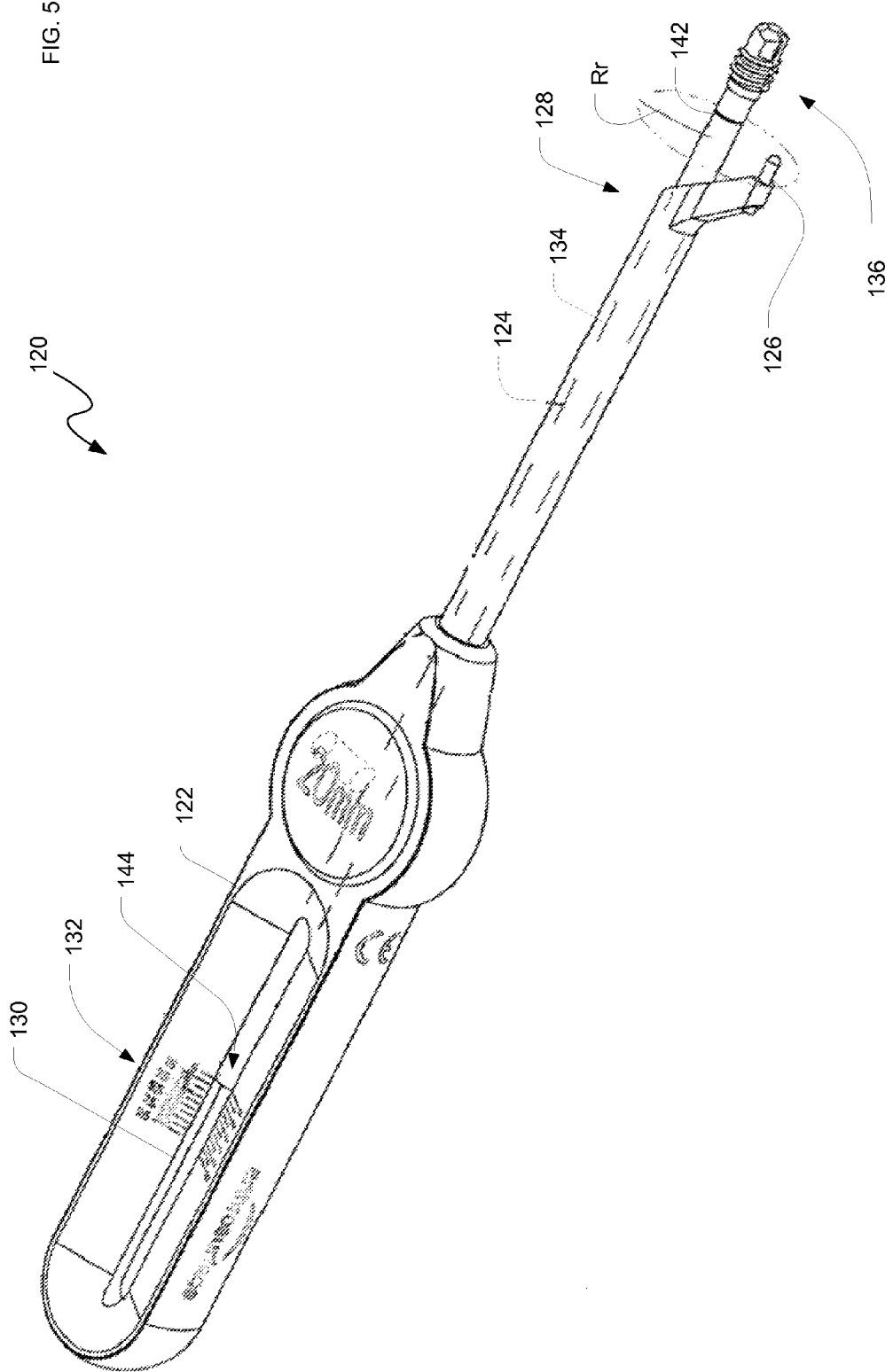
FIG. 5 illustrates a perspective view of one embodiment of a measuring device.
Figure 8:
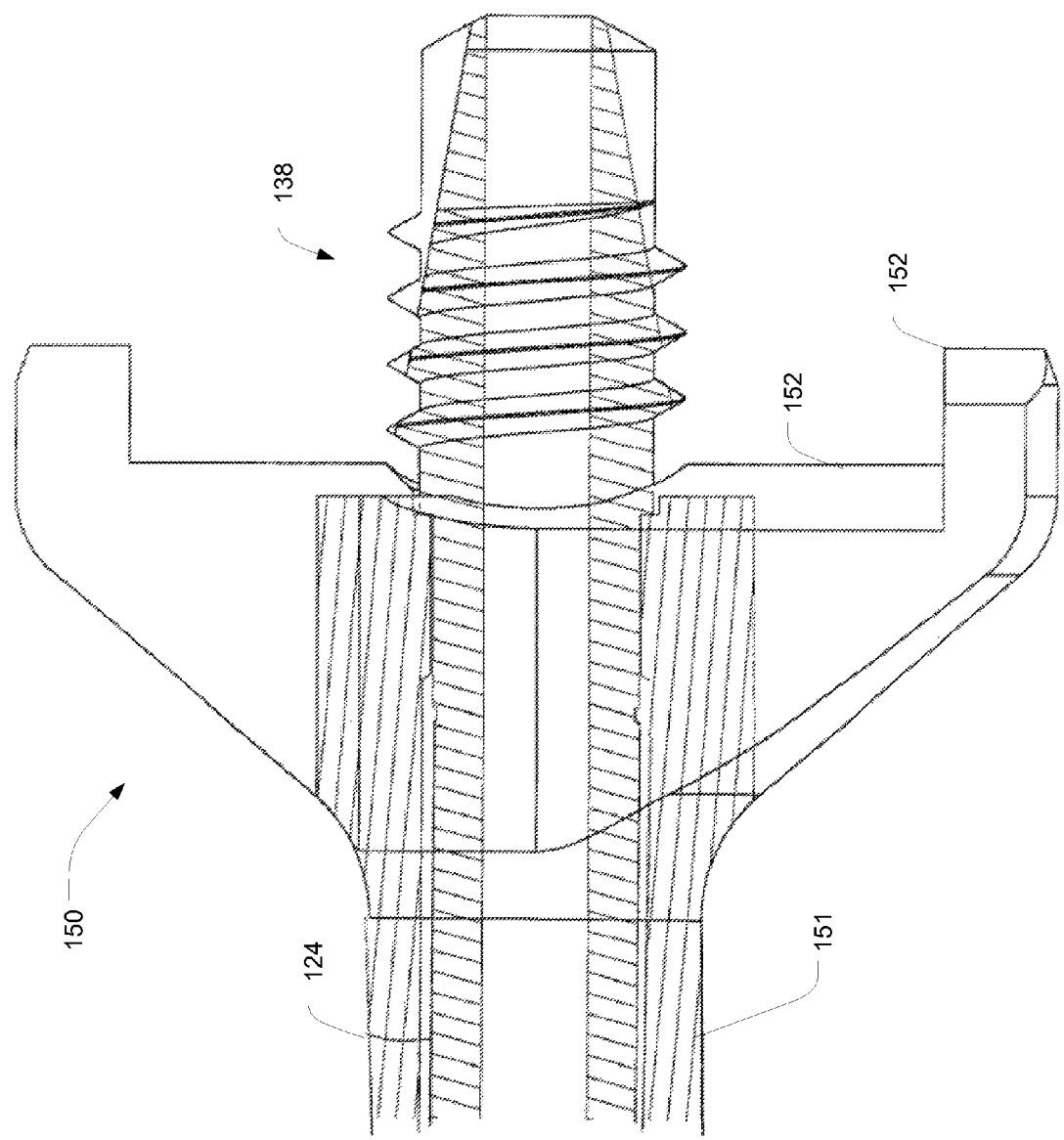
FIG. 8 is a close-up of one embodiment of a reamer.

FIG. 5 depicts a measuring device 120 consistent with another aspect of the present disclosure. Measuring device 120 may be used to obtain or map a plurality of points on a patient's articular surface. Instead of a separate screw element, however, the measuring device 120 of the present embodiment may include an integrally formed tap (described below) that may be readily advanced and removed into and from the bone. The measuring device 120 may comprise a housing 122 defining a longitudinally disposed passageway 124 therein. The housing 122 may comprise an outrigger 126 extending generally outwardly from the distal end 128 of the housing 122 a predefined radial distance Rr from the longitudinal axis of the housing 122. The housing 122 may also include a window or aperture 130 having a plurality of measurement markings/indicia (generally indicated by 132) for generating a measurement as will be described below.

The measuring device 120 may also feature a guide pin 134, as shown in FIGS. 5-8, configured to be rotatably disposed within the longitudinally disposed passageway 124 of the housing 112. A distal end 136 of the guide pin 134 (best seen in FIG. 7) may include a tap 138 for boring into the articular surface. The tap 138 may include fluted regions 139 and cutting edges 140 which allow the guide pin 134 to be self drilling and self tapping.

The distal end 136 of the guide pin 134 may be inserted into the articular surface by rotating the guide pin 134. This may be preformed by hand, but may optionally include the use of a drill or the like. As the guide pin 134 is rotated, the tap 138 bores and threads a hole into the articular surface to secure the guide pin 134 relative to the articular surface. The depth which the guide pin 134 is inserted into the articular surface may be determined by one or more visual indicia located on the guide pin 134. For example, the guide pin 134 may feature an indentation or indicia (such as, but not limited to, a laser marking or the like) 142 extending generally radially inwardly a predetermined distance proximate the distal end 136 of the guide pin 134. In practice, a surgeon may screw the guide pin 134 into the articular surface until the indentation 142 is substantially coplanar with the articular surface.

Once the guide pin 134 is inserted into the articular surface proximate the region to be measured, the housing 122 of the measuring device 120 may be placed axially along the guide pin 134. The measuring device 120 may be rotated about the guide pin 134 until the outrigger 126 is proximate the area to be measured. Measurements may be obtained by contacting the outrigger 126 with the articular surface and reading which of the marking indicia 132 along the window 130 of the housing 122 are aligned with a visual indicia on the guide pin 134 (such as the proximate end 144, markings and/or indentations on the guide pin 134). This process may be repeated until the desired number of measurements are obtained.

Once the desired number of measurements are taken, the housing 122 of the measuring device 120 may be removed from the guide pin 134. Using the guide pin 134 extending from the articular surface, a reamer 150, shown in FIG. 8, may be axially aligned along the guide pin 134. The reamer 150 may be used to excise a region of the articular surface and may comprise a shaft 151 which may be coupled to a drill device (such as, but not limited to, a hand or power operated drill). The reamer 150 may be rotated about the guide pin 134 such that the cutting surfaces 152 of the reamer excise a portion of the articular surface.

As mentioned above, the present disclosure is not intended to be limited to a system or method which must satisfy one or more of any stated or implied object or feature of the present disclosure and should not be limited to the preferred, exemplary, or primary embodiment(s) described herein. The foregoing description of a preferred embodiment of the present disclosure has been presented for purposes of illustration and description. It is not intended to be exhaustive or to limit the present disclosure to the precise form disclosed. Obvious modifications or variations are possible in light of the above teachings. The embodiment was chosen and described to provide the best illustration of the principles of the present disclosure and its practical application to thereby enable one of ordinary skill in the art to utilize the present disclosure in various embodiments and with various modifications as is suited to the particular use contemplated. All such modifications and variations are within the scope of the present disclosure.

What is claimed is:

1. An implant for replacing a portion of an articular surface of a bone comprising:
    at least a first and a second segment each comprising a truncated, generally arcuate perimeter corresponding to a first and a second overlapping generally circular excision site to be formed in said articular surface, respectively, wherein said second segment partially overlaps said first segment on a first end of said first segment, and wherein said first and said second segments comprise a bone contacting surface and a load bearing surface, said load bearing surface comprising curvature corresponding to a curvature of said replaced portion of said articular surface of said bone.

2. The implant of claim 1, wherein said bone contacting surface comprises a first mounting feature configured to secure said implant to said bone.

3. The implant of claim 1, further comprising a third segment comprising a truncated, generally arcuate perimeter corresponding to a third generally circular excision site formed in said articular surface, said third generally circular excision site overlapping with said second generally circular excision site, wherein said third segment partially overlaps said first segment on a second end of said first segment, said third segment comprising a portion of said bone contacting surface and said load bearing surface.

4. The implant of claim 2, wherein said first mounting feature is configured to securely engage with a fastening element, said fastening element configured to be secured to said bone.

5. The implant of claim 4, wherein said fastening element includes a mounting screw.

6. The implant of claim 4, wherein said first mounting feature includes a tapered opening configured to engage with a tapered post of said fastening element.

7. The implant of claim 4, wherein said first mounting feature includes a tapered post configured to engage with a tapered opening of said fastening element.

8. The implant of claim 2, wherein said bone contacting surface further comprises a second mounting feature configured to secure said implant to said bone.

9. The implant of claim 8, wherein said second mounting feature includes a protrusion extending generally outwardly from said bone facing surface.

10. The implant of claim 3, wherein said bone facing surface of said first segment includes a first mounting feature and wherein said bone facing surface of said second segment includes a second mounting feature.

11. The implant of claim 3, wherein said bone facing surface of said third segment includes a third mounting feature.

12. The implant of claim 11, wherein said first, said second, and said third mounting features are axially aligned with said first, said second, and said third overlapping generally circular excision site formed in said articular surface, respectively.

13. The implant of claim 1, wherein said load bearing surface comprises an anterior-posterior (AP) curvature and a medial lateral (ML) curvature.

14. The implant of claim 1, wherein said curvature of said load bearing surface comprises at least two tangential curves of said portion of said articular surface of said bone, said tangential curves having different radii of curvature.

15. The implant of claim 3, wherein said bone facing surface of said first segment includes a first mounting feature.

16. The implant of claim 1, wherein said first and said second segments of said bone facing surface each have a non-planar surface.

17. The implant of claim 1, wherein said first and said second bone facing surfaces are further defined by a first and a second lip, respectively, each of said lips defining a portion of an outer perimeter of said implant and at least one recess, wherein said first lip partially intersects with said second lip.

18. The implant of claim 1, wherein at least a portion of said first and said second bone facing surfaces are generally symmetrical about a center of said first and said second generally circular excision site.

19. The implant of claim 1, wherein truncated, generally arcuate perimeters of said first and said second segments each comprise a center corresponding to said first and said second generally circular excision site, respectively.

20. A method for replacing a portion of an articular surface, said method comprising:
reaming a first portion of said articular surface to form a first generally circular excision site;
reaming a second portion of said articular surface to form a second generally circular excision site partially overlapping said first generally circular excision site; and
selecting an implant having first and second segments each comprising a truncated, generally arcuate perimeter corresponding to said first and said second overlapping generally circular excision sites, respectively, wherein said second segments partially overlaps said first segment on a first end of said first segment, and wherein said first and said second segments comprise a bone contacting surface and a load bearing surface, said load bearing surface comprising curvature corresponding to a curvature of said replaced portion of said articular surface of said bone.

21. The method of claim 20, further comprising a placing a drill guide onto said articular surface and establishing a plurality of axes in said articular surface corresponding to said second and said third excision sites using said drill guide.

22. The method of claim 21, wherein reaming said second and said third excision sites comprises advancing at least one reamer along said plurality of axes towards said articular surface, wherein said at least one reamer is rotated about said plurality of axes.

23. The method of claim 20, further comprising securing said implant to bone beneath said articular surface.

24. The method of claim 23, wherein securing said implant further comprises securing a fastening element into said bone and securing said implant to said fastening element.

25. The method of claim 24, wherein said fastening element comprises a screw, and wherein securing said fastening element into said bone further comprises advancing said screw into said bone.

26. The method of claim 24, wherein said implant and said fastening element are secured using a tapered frictional coupling.

27. The method claim 20, further comprising reaming a third portion of said articular surface to form a third generally circular excision site partially overlapping said first generally circular excision site on a second end of said first segment; and
wherein said selecting further comprises selecting an implant having first, second, and second third segments each comprising a truncated, generally arcuate perimeter corresponding to said first, said second, and said second third overlapping generally circular excision sites, respectively.

28. An implant for replacing a portion of an articular surface of a bone comprising:
a bone facing surface comprising at least a first, a second, and a third segment each corresponding to at least a first, a second, and a third intersecting excision site to be formed in said articular surface, respectively, wherein said first, said second, and said third segments of said bone facing surface each have a non-planar surface, and wherein said bone facing surface further comprises a plurality of fixation elements configured to secure said implant to said excision sites; and a load bearing surface comprising a curvature generally corresponding to a curvature of said replaced portion of said articular surface of said bone, wherein said curvature of said load bearing surface comprises at least two tangential curves of said replaced portion of said articular surface of said bone, said tangential curves having different radii of curvature.

29. The implant of claim 28, wherein said implant is a femoral implant, and wherein said curvature of said load bearing surface generally corresponds to a portion of a femoral articular surface.

30. The implant of claim 29, wherein said load bearing surface comprises an anterior-posterior (AP) curvature and a medial lateral (ML) curvature.

31. The implant of claim 30, wherein said at least two tangential curves are disposed along an anterior-posterior (AP) surface of said femur.

32. The implant of claim 28, wherein at least one of said fixation elements includes a protrusion extending generally outwardly from said bone facing surface.

33. The implant of claim 28, wherein said first, said second, and said third segment of said bone facing surface each includes at least one of said plurality of fixation elements.

34. The implant of claim 28, wherein said curvature of said load bearing surface comprises a first, a second, and a third tangential curves each extending along a portion of said replaced portion of said articular surface of said bone, wherein said portion of said second curve is approximately tangential to said portion of said first curve and said portion of said third curve at opposite ends thereof.

35. The implant of claim 28, wherein said curvature of said load bearing surface comprises a first, a second, and a third tangential curves each extending along a portion of said replaced portion of said articular surface of said bone, wherein said portion of said second curve is approximately tangential to said portion of said first curve and said portion of said third curve at opposite ends thereof.

36. An implant for replacing a portion of an articular surface of a bone comprising:
a bone facing surface comprising a first segment which intersects with a second and a third segment, wherein said first, said second, and said third segment of said bone facing surface each correspond to at least a first, a second, and a third intersecting excision site to be formed in said articular surface, respectively, said first, said second, and said third segments of said bone facing surface each having a non-planar surface and each including at least one fixation element configured to secure said implant to said bone; and a load bearing surface comprising an anterior-posterior (AP) curvature and a medial lateral (ML) curvature corresponding to an AP and a ML curvature of said replaced portion of said articular surface of said bone, respectively, wherein said AP curvature of said load bearing surface comprises at least two tangential curves of said replaced portion of said articular surface of said bone, said tangential curves having different radii of curvature.

37. The implant of claim 36, wherein said implant is a femoral implant, and wherein said curvature of said load bearing surface generally corresponds to a portion of a femoral articular surface.

38. The implant of claim 36, wherein at least one of said fixation elements includes a protrusion extending generally outwardly from said bone facing surface.

39. An implant for replacing a portion of an articular surface of a bone comprising:
a bone facing surface comprising a first, a second, and a third segment having a periphery defined by a first, a second, and a third lip, respectively, each of said lips defining a portion of an outer perimeter of said implant and at least one recess, wherein said first lip partially intersects with said second and said third lips;

a plurality of fixation elements extending outwardly from said bone facing surface configured to secure said implant to said bone; and a load bearing surface comprising a curvature generally corresponding to a curvature of said replaced portion of said articular surface of said bone, wherein said curvature of said load bearing surface comprises at least two tangential curves of said replaced portion of said articular surface of said bone, said tangential curves having different radii of curvature.

40. The implant of claim 39, wherein said load bearing surface comprises an anterior-posterior (AP) curvature and a medial lateral (ML) curvature, and wherein said at least two tangential curves are disposed along an anterior-posterior (AP) surface of said femur.

41. The implant of claim 40, wherein said curvature of said load bearing surface comprises a first, a second, and a third tangential curves each extending along a portion of said replaced portion of said articular surface of said bone, wherein said portion of said second curve is approximately tangential to said portion of said first curve and said portion of said third curve at opposite ends thereof.

42. An implant for replacing a portion of an articular surface of a bone comprising:
a bone facing surface comprising a plurality of segments each corresponding to a respective one of a plurality of intersecting excision sites to be formed in said articular surface, wherein said plurality of segments of said bone facing surface each have a non-planar surface, and wherein said bone facing surface further comprises a plurality of fixation elements configured to secure said implant to said plurality of overlapping excision sites; and a load bearing surface comprising a curvature generally corresponding to a curvature of said replaced portion of said articular surface of said bone, wherein said curvature of said load bearing surface comprises at least two tangential curves of said replaced portion of said articular surface of said bone, said tangential curves having different radii of curvature.

\* \* \* \* \*

UNITED STATES PATENT AND TRADEMARK OFFICE
CERTIFICATE OF CORRECTION

| | |
|---|---|
| PATENT NO. | : 8,864,827 B2 |
| APPLICATION NO. | : 13/470678 |
| DATED | : October 21, 2014 |
| INVENTOR(S) | : Steven W. Ek |

It is certified that error appears in the above-identified patent and that said Letters Patent is hereby corrected as shown below:

Title Page, item (63):
On page 1, in column 1 (Related U.S. Application Data), Line 2, delete "and" and insert -- which is --, therefor.

Title Page, item (56):
On page 7, in column 1 (Other Publications), Line 22, delete "10/99,453" and insert -- 10/994,453 --, therefor.
On page 7, in column 2 (Other Publications), Line 21, delete "Nonarthoplasty" and insert -- Nonarthroplasty --, therefor.
On page 10, in column 1 (Other Publications), Line 12, delete "patnet" and insert -- patent --, therefor.
On page 10, in column 1 (Other Publications), Line 14, delete "patnet" and insert -- patent --, therefor.
On page 10, in column 1 (Other Publications), Line 16, delete "patnet" and insert -- patent --, therefor.
On page 10, in column 1 (Other Publications), Line 18, delete "patnet" and insert -- patent --, therefor.
On page 10, in column 2 (Other Publications), Line 69, delete "Jorunal" and insert -- Journal --, therefor.
On page 11, in column 1 (Other Publications), Line 5, delete "pges" and insert -- pages --, therefor.
On page 11, in column 1 (Other Publications), Line 11, delete "Experimantal" and insert -- Experimental --, therefor.
On page 11, in column 1 (Other Publications), Line 21, delete "Experriencesl" and insert -- Experiences --, therefor.
On page 11, in column 1 (Other Publications), Line 41, delete "Medicing" and insert -- Medicine --, therefor.
On page 11, in column 1 (Other Publications), Line 41, delete "Natinal" and insert -- National --, therefor.
On page 11, in column 1 (Other Publications), Line 45, delete "Arthroscipic" and insert -- Arthroscopic --, therefor.
On page 11, in column 2 (Other Publications), Line 31, delete "Repoort" and insert -- Report --, therefor.

Signed and Sealed this
Nineteenth Day of May, 2015

Michelle K. Lee
*Director of the United States Patent and Trademark Office*

In the Claims

In column 10, line 20, in Claim 20, delete "segments" and insert -- segment --, therefor.

In column 10, line 48, in Claim 27, after "method" insert -- of --, therefor.